US008710011B2

(12) United States Patent
Garcia Sanz et al.

(10) Patent No.: US 8,710,011 B2
(45) Date of Patent: Apr. 29, 2014

(54) COSMETIC OR PHARMACEUTICAL PEPTIDES CONTAINING UNCODED AMINO ACIDS AND THEIR USE IN THE TREATMENT AND/OR CARE OF THE SKIN, MUCOUS MEMBRANES, OR SCALP

(75) Inventors: Nuria Garcia Sanz, Alicante (ES); Wim Van Den Nest, Barcelona (ES); Cristina Carreno Serraima, Barcelona (ES); Antonio Ferrer Montiel, Alicante (ES); Juan Cebrian Puche, Barcelona (ES); Nuria Alminana Domenech, Barcelona (ES)

(73) Assignee: Lipotec, S.A., Gava, Barcelona (ES)

( * ) Notice: Subject to any disclaimer, the term of this patent is extended or adjusted under 35 U.S.C. 154(b) by 336 days.

(21) Appl. No.: 13/201,374

(22) PCT Filed: Feb. 16, 2010

(86) PCT No.: PCT/EP2010/000937
§ 371 (c)(1),
(2), (4) Date: Aug. 12, 2011

(87) PCT Pub. No.: WO2010/091893
PCT Pub. Date: Aug. 19, 2010

(65) Prior Publication Data
US 2011/0300199 A1     Dec. 8, 2011

(30) Foreign Application Priority Data

Feb. 16, 2009  (ES) .................................. 200900426

(51) Int. Cl.
| | | |
|---|---|---|
| *A61K 38/00* | (2006.01) | |
| *A61K 38/04* | (2006.01) | |
| *A61K 38/07* | (2006.01) | |
| *A61K 38/08* | (2006.01) | |
| *A61K 8/00* | (2006.01) | |
| *A61K 8/64* | (2006.01) | |
| *C07K 7/04* | (2006.01) | |
| *C07K 7/06* | (2006.01) | |
| *A61Q 19/00* | (2006.01) | |
| *A61Q 19/08* | (2006.01) | |

(52) U.S. Cl.
CPC ................. *A61K 38/00* (2013.01); *A61K 38/04* (2013.01); *A61K 38/07* (2013.01); *A61K 38/08* (2013.01); *A61K 8/00* (2013.01); *A61K 8/64* (2013.01); *C07K 7/04* (2013.01); *C07K 7/06* (2013.01); *A61Q 19/00* (2013.01); *A61Q 19/08* (2013.01)
USPC ....... 514/18.6; 514/18.7; 514/18.8; 514/21.7; 514/21.8; 514/21.9; 424/401; 424/59; 530/329; 530/330

(58) Field of Classification Search
None
See application file for complete search history.

(56) References Cited

U.S. PATENT DOCUMENTS

| | | |
|---|---|---|
| 4,643,991 A | 2/1987 | Digenis et al. |
| 4,665,053 A | 5/1987 | Robert et al. |
| 5,008,245 A | 4/1991 | Digenis et al. |
| 5,162,307 A | 11/1992 | Digenis et al. |
| 5,189,178 A | 2/1993 | Galardy et al. |
| 5,922,319 A | 7/1999 | Digenis et al. |
| 6,238,674 B1 | 5/2001 | Renimel et al. |
| 6,395,261 B1 | 5/2002 | Laforet |
| 6,645,477 B1 | 11/2003 | Jarrousse et al. |
| 7,211,278 B2 | 5/2007 | Tsuji et al. |

FOREIGN PATENT DOCUMENTS

| | | |
|---|---|---|
| EP | 0126009 | 11/1984 |
| EP | 1076549 | 9/2004 |
| EP | 1892247 | 2/2008 |
| JP | 11246386 | 9/1999 |
| JP | 11279041 | 10/1999 |
| JP | 2000072649 | 3/2000 |
| WO | 9808815 | 3/1998 |
| WO | 9836742 | 8/1998 |
| WO | 2007042254 | 4/2007 |
| WO | 2007113356 | 10/2007 |
| WO | 2007129952 | 11/2007 |

OTHER PUBLICATIONS

Hipler et al. Biofunctional Textiles and the Skin 2006, vol. 33, 10 Pages, "Current Problems in Dermatology."
Lloyd-Williams et al. Chemical Approaches to the Synthesis of Peptides and Proteins 1997, 78 Pages, "Solid-Phase Peptide Synthesis."
Smith et al. 1999, 5th edition, 111 Pages, "March's Advanced Organic Chemistry Reactions, Mechanisms, and Structure."
Rink, Tetrahedron Letters 1987, vol. 28, No. 33, p. 3787-3790, "Solid-Phase Synthesis of Protected Peptide Fragements Using a Trialkoxy-Diphenyl-Methylester Resin."
Miyoshi et al. The Journal of Dermatology 2005, vol. 32, p. 346-353, "Beneficial Effects of Tissue Inhibitor of Metalloproteinases-2 (TIMP-2) on Chronic Dermatitis."
Abraham et al. Current Vascular Pharmacology 2005, vol. 3, p. 369-379, "Connective Tissue Remodeling: Cross-Talk between Endothelins and Matrix Metalloproteinases."
Brincat et al. Obstetrics and Gynecology / Postmenopausal Changes Dec. 1987, vol. 70, No. 6, p. 840-845, "S Study of the Decrease of Skin Collagen Content, Skin Thickness, and Bone Mass in the Postmenopausal Woman."
Tsukahara et al. British Journal of Dermatology 1999, vol. 140, p. 1048-1053, "All-trans retinoic acid promotes the repair of tortuosity of elastic fibres in rat skin."

(Continued)

*Primary Examiner* — Kevin S Orwig
(74) *Attorney, Agent, or Firm* — Fay Sharpe LLP

(57) ABSTRACT

Peptides of general formula (I): $R_1-W_p-X_n-AA1-AA_2-AA_3-AA_4-Y_m-R_2$ their stereoisomers, mixtures thereof, and/or their cosmetically or pharmaceutically acceptable salts, a method of preparation, cosmetic or pharmaceutical compositions containing them and their use for the treatment, prevention and/or care of conditions, disorders and/or diseases of the skin, mucous membranes and/or scalp.

25 Claims, No Drawings

(56) References Cited

OTHER PUBLICATIONS

Tassabehji et al. Human Molecular Genetics 1998, vol. 7, No. 6, p. 1021-1028, "An elastin gene mutation producing abnormal tropoelastin and abnormal elastic fibres in a patient with autosomal dominant cutis laxa."
Tsukahara et al. British Journal of Dermatology 2001, vol. 144, p. 452-458, "Carbon dioxide laser treatment promotes repair of the three-dimensional network of elastic fibres in rat skin."
Imokawa et al. The Journal of Investigative Dermatology Aug. 1995, vol. 105, No. 2, p. 254-258, "Degree of Ultraviolet-Induced Tortuosity of Elastic Fibers in Rat Skin is Age Dependent."
Debelle et al. The International Journal of Biochemistry and Cell Biology 1999, vol. 31, p. 261-272, "Elastin: molecular description and function."
Antonicelli et al. Current Topics in Developmental Biology 2007, vol. 79, p. 99-155, "Elastin-Elastases and Inflamm-Aging."
Wiedow et al. The Journal of Investigative Dermatology Sep. 1992, vol. 99, No. 3, p. 306-309, "Lesional Elastase Activity in Psoriasis, Contact Dermatitis, and Atopic Dermatitis."
Bellingham et al. Biochimica et Biophysica Acta 2001, vol. 1550, p. 6-19, "Self-aggregation characteristics of recombinantly expressed human elastin polypeptides."
Reynolds et al. J. R. Coll. Surg. Edinb. Jun. 1997, vol. 42, p. 154-160, "The functional balance of metalloproteinases and inhibitors in tissue degradation: relevance to oral pathologies."
Faury, Pathol. Biol. 2001, vol. 49, p. 310-325, "Function-structure relationship of elastic arteries in evolution: from microfibrils to elastin and elastic fibres."
Csiszar, Progress in Nucleic Acid Research and Molecular Biology 2001, vol. 70, p. 1-32, "Lysyl Oxidases: A Novel Multifunctional Amine Oxidase Family."
Woodbury et al. Acta. Derm. Venereol. (Stockh) 1994, vol. 74, p. 15-17, "Rapid Assay of the Anti-inflammatory Activity of Topical Corticosteroids by inhibition of a UVA-induced neutrophil Infiltration in Hairless Mouse Skin."
Dick et al. Acta. Dermatovener (Stockholm) 1976, vol. 56, p. 279-282, "Study of Elastolytic Activity of Propionibacterium Acnes and Staphylococcus epidermis in Acne Vulgaris and in Normal Skin."
Fauli. Treated Galenic Pharmacy 1993, "Pharmaceutical Technology", English translation of first paragraph, 8 Pages.
Dweck. R.G. Harry Cosmeticology 8th edition, 2000, 27 Pages, "Botanicals in Cosmetics & Toiletries."
Remington, 21st edition, 2005, "The Science and Practice of Pharmacy." 60 Pages.
Joint Commussion on Biochemical Nomenclature Eur. J. Biochem. 1984, vol. 138, p. 9-37, "Nomenclature and Symbolism for Amino Acids and Peptides."
International Search Report for PCT/EP2010/000937, Completed by the European Patent Office on May 20, 2010, 3 Pages.
Kaiser et al. Anal. Biochem. 1970, vol. 34, p. 595-598, "Color Test for Detection of Freee Terminal Amino Groups in the Solid-Phase Synthesis of Peptides."
Malcolm et al. Journal of Controlled Release 2004, vol. 97, p. 313-320, "Controlled release of model antibacterial drug from a novel self-lubricating silicone biomaterial."
Nelson. International Journal of Pharmaceutics 2002, vol. 242, p. 55-62, "Application of microencapsulation in textiles."
Schabb. Happi, May 1986, p. 84-86, "Impregnating Fabrics With Microcapsules."
Wang. Journal of the American Chemical Society Feb. 21, 1973, vol. 95, No. 4, p. 1328-1333 "p-Alkoxybenzyl Alcohol Resin and P-Alkoxybenzyloxycarbonylhydrazide Resin for Solid Phase Synthesis of Protected Peptide Fragments."
Albericio et al. J. Org. Chem. 1990, vol. 55, p. 3730-3743, "Preparation and Application of the 5-(4-(9-Fluorenylmethyloxycarbonyl)aminomethyl-3,5-dimethoxyphenoxy)- valeric Acid (PAL) Handle for the Solid-Phase Synthesis of C-Terminal Peptide Amides under Mild Conditions 1-3."
Barlos et al. Tetragedron Letters 1989, vol. 30, No. 30, p. 3947-3950, "Veresterung Von Partiell Geschutzten Peptid-Fragmenten Mit Harzen. Einsatz Von 2-Chlortritylchlorid Zur Synthese Von Leu 15—Gastrin I."
Barlos et al. Tetrahedron Letters 1989, vol. 30, No. 30, p. 3943-3946, "Darstellung Geschutzter Peptid-Fragmente Unter Einsatz Substituierter Triphenylmethyl-Harze."
Matsueda et al. Peptides 1981, vol. 2, p. 45-50, "A p-Methylbenzhydrylamine Resin for Improved Solid-Phase Syntheis of Peptide Amides."
Atherton et al. The Practical Approach Series 1989, All together 17 Pages, "Solid Phase peptide synthesis, a practical approach."
Greene et al. Protective Groups in Organic Synthesis third edition, 1999, "The Role of Protective Groups in Organic Synthesis.", All together 20 Pages.
Lloyd-Williams et al. Tetragedron 1993, vol. 49, No. 48, p. 11065-11133, "Tetrahedron Report Number 347, Convergent Solid-Phase Peptide Synthesis."
Bodanszky et al. The Practice of Peptide Synthesis second edition 1984, "Activation and Coupling", All together 54 Pages.
Stewart et al. Solid Phase Peptide Synthesis 1984 second edition 1984, "The Chemistry of Solid Phase Peptide Synthesis.", All together 20 Pages.
Berge et al. Journal of Pharmaceutical Sciences Jan. 1977, vol. 66, No. 1, p. 1-19, "Review Article, Pharmaceutical Salts."
Traurig et al. Diabetes Nov. 2006, vol. 55, p. 3160-3165, "Differential Expression of Matrix Metalloproteinase 3 (MMP3) in Preadipocytes/Stromal Vascular Cells From Nonobese Nondiabetic Versus Obese Nondiabetic Pima Indians."
Herouy et al. Journal of Dermatological Sciences 2001, vol. 25, p. 198-205, "Inflammation in stasis dermatitis upregulares MMP-1, MMP-2 and MMP-13 expression."
Sato et al. Cancer Sci. Apr. 2005, vol. 96, No. 4, p. 212-217 "Roles of membrane-type matrix metalloproteinase-1 in tumor invasion and metastasis."
Ntayi et al. Pathologic Biologie 2004, vol. 52, p. 154-159, "Involvement of matrix metalloproteinases (MMPs) in cutaneous melanoma progression."
Suomela et al. Acta Derm Venereol 2003, vol. 83, p. 108-114, "Matrix Metalloproteinase-19 is Expressed by Keratinocytes in Psoriasis."
Flisiak et al. JEADV 2005, vol. 19, p. 18-421, "Effect of psoriasis treatment on plasma concentrations of metalloproteinase-1 and tissue inhibitor of metalloproteinases-1."
Lahmann et al. The Lancet Mar. 24, 2001, vol. 357, p. 935-936, "Matrix metalloproteinase-1 and skin ageing in smokers."
Rittie et al. Ageing Research Reviews 2002, vol. 1, p. 705-720, "UV-light-induced signal cascades and skin aging."
Fisher et al. The Journal of Investigative Dermatology Aug. 2001, vol. 117, No. 2, p. 219-226, "Ultraviolet Irrdiation Increases Matrix Metalloproteinase-8 Protein in Human Skin in Vivo."
Fisher et al. Nature Jan. 25, 1996, vol. 379, p. 335-339, "Molecular basis of sun-induced premature skin ageing and retinoid antagonism."
Freinkel et al. The Biology of Skin 2001, p. 32-35, "Structure and Function of the Skin: Overview of the Epidermis and Dermis."
Devillers et al. Clinical and Experimental Dermatology 2007, vol. 32, p. 311-313, "Elevated levels of plasma matrix metalloproteinase-9 in patients with atopic dermatitis: a pilot study."
Liu et al. The Journal of Clinical Investigation Jan. 2000, vol. 105, No. 1, p. 113-123, "A critical role for neutrophil elastase in experimental bullous pemphigoid."
Sapadin et al. J. Am. Acad. Dermatol. 2006, vol. 54, No. 2, p. 258-265, "Tetracyclines: Nonantibiotic properties and their clinical implications."
Rogalski et al. Journal of Investigative Dermatology Jan. 2002, vol. 118, No. 1, p. 49-54, "Human Leukocyte Elastase Induces Keratinocyte Proliferation In Vitro and In Vivo."
Papakonstantinou et al. The Journal of Investigative Dermatology Oct. 2005, vol. 125, p. 673-684, "Matrix Metalloproteinases of Epithelial Origin in Facial Sebum of Patients with Acne and their Regulation of Isotretinoin."

(56) References Cited

OTHER PUBLICATIONS

Kerkela et al. Experimental Dermatology 2003, vol. 12, p. 109-125, "Matrix metalloproteinases in tumor progression: focus on basal and squamous cell skin cancer."

Kahari et al. Exp. Dermatol. 1997, vol. 6, p. 199-213, "Matrix metalloproteinases in skin."

Tsukahara et al. The Journal of Investigative Dermatology Sep. 2001, vol. 117, No. 3, p. 671-677, "Selective Inhibition of Skin Fibroblast Elastase Elicits a Concentration-Dependent Prevention of Ultraviolet B-Induced Wrinkle Formation."

Fisher et al. The New England Journal of Medicine Nov. 13, 1997, vol. 337, No. 20, p. 1419-1428, "Pathophysiology of Premature Skin Aging Induced by Ultraviolet Light."

Culav et al. Physical Therapy 1999, vol. 79, p. 308-319, "Connective Tissues: Matrix Composition and its Relevance to Physical Therapy.".

Aumailley et al. J. Mol. Med. 1998, vol. 76, p. 253-265, "Structure and biological activity of the extracellular matrix."

Kielty et al. Journal of Cell Science 2002, vol. 115, No. 14, p. 2817-2828, "Elastic fibres."

Kullmann. The Journal of Biological Chemistry Issue of Sep. 10, 1980, vol. 255, No. 17, p. 8234-8238, "Proteases as Catalysts for Enzymic Syntheses of Opioid Peptides."

Borel et al. The Journal of Biological Chemistry 2001, vol. 276, No. 52, p. 48944-48949, "Lysyl Oxidase-like Proetin from Bovine Aorta."

Brown-Augsburger et al. The Journal of Biological Chemistry Issue of Jul. 28, 1995, vol. 270, No. 30, p. 17778-17783, "Identification of an Elastin Cross-linking Domain That Joins Three Peptide Chains."

Watson et al. The Journal of Investigative Dermatology, May 1999, vol. 112, No. 5, p. 782-787, "Fibrillin-Rich Microfibrils are Reduced in Photoaged Skin. Distribution at the Dermal-Epidermal Junction."

Jarrousse et al. International Journal of Dermatology 2001, vol. 40, p. 385-392. "Identification of clustered cells in human hair follicle responsible for MMP-9 gelatinolytic activity: consequences for the regulation of hair growth."

COSMETIC OR PHARMACEUTICAL PEPTIDES CONTAINING UNCODED AMINO ACIDS AND THEIR USE IN THE TREATMENT AND/OR CARE OF THE SKIN, MUCOUS MEMBRANES, OR SCALP

CROSS-REFERENCE TO RELATED APPLICATION

This application is the U.S. national phase of PCT Appln. No. PCT/EP2010/000937 filed Feb. 16, 2010 which claims priority to Spanish application P200900426 filed Feb. 16, 2009, the disclosures of which are incorporated in their entirety by reference herein.

FIELD OF THE INVENTION

This invention relates to peptides capable of inhibiting elastase activity and/or stimulating collagen synthesis in the skin, mucous membranes and/or scalp and cosmetic or pharmaceutical compositions containing these peptides and their use in the treatment and/or care of skin, mucous membranes, and/or scalp, preferably for the treatment, prevention and/or care of the conditions, disorders and/or diseases of the skin, mucous membranes, and/or scalp which result from elastase activity and/or which benefit from stimulation of collagen synthesis.

BACKGROUND OF THE INVENTION

The skin is made of two layers, dermis and epidermis. The epidermis is the outermost layer and is composed of keratinocytes, melanocytes and Langerhans cells. The main cell population in the epidermis consists of keratinocytes, which form a keratinized layer that is constantly renewed. Its function is to protect against external agents, whether physical, chemical or pathogenic. The dermis is located more internally and is attached to the epidermis through the basement membrane. It consists of fibroblasts, adipocytes and macrophages, is irrigated by blood vessels and has many nerve endings responsible for transmitting sensations of touch and temperature. The hair follicles lay in the dermis, as well as the sweat, sebaceous and apocrine glands, whose function is to maintain the integrity and elasticity of the skin. These properties are given by their extracellular matrix, composed of proteins secreted by the fibroblasts.

The proteins of the extracellular matrix (ECM) are classified into two groups: glycosaminoglycans and fibrous proteins. Glycosaminoglycans (GAG) are unbranched chains resulting from the polymerization of aminosugar disaccharides. Due to their chemical properties and their large number of negative charges, GAG form bulky structures which tend to attract large amounts of water, giving the ECM resistance to compression. Fibrous proteins have structural and adhesive functions and are mainly two: elastin and collagen, which are responsible for the mechanical properties of the tissues such as the ability to resist tension, compression, extensibility and torsion.

The elasticity and resilience properties of ECM are due to a network of elastic fibers. Structurally, the elastic fibers are composed of an elastin core covered by a pod of microfibrils of approximately 10 nm in diameter. Microfibrils are composed of fibrillin and microfibril-associated glycoprotein (MAGP). The assembly of the elastic fibers is sequential, microfibrils appearing first and forming a skeleton on which elastin is deposited. Elastin is a highly hydrophobic protein, composed of approximately 750 amino acid residues and is originated from a hydrosoluble precursor, tropoelastin, which is secreted into the extracellular space by the fibroblasts. Elastin fibers are the result of the assembly and crosslinking of tropoelastin monomers near the plasma membrane of the fibroblasts.

The tropoelastin molecule is synthesized in soluble form, with a molecular weight of about 70 kDa, and in its sequence presents hydrophobic domains alternating with crosslinking domains [Brown-Augsburger P., Tisdale C., Broekelmann T., Sloan C. and Mecham R. P. (1995) "*Identification of an elastin crosslinking domain that joins three peptide chains*" *J. Biol. Chem.* 270:17778-17783]. The hydrophobic domains are repetitions of peptides from two to nine amino acids rich in proline, alanine, valine, leucine, isoleucine and glycine, among which valine and glycine are especially abundant [Debelle L. and Tamburro A. M. (1999) "*Elastin: molecular description and function*" *Int J. Biochem. Cell Biol.* 31:261-272]. The interactions between hydrophobic domains are important in the assembly and essential for the elasticity of the molecule [Bellingham C. M., Woodhouse K. A., Robson P., Rothstein S. J. and Keeley F. W. (2001) "*Self-aggregation of recombinantly expressed human elastin polypeptides*" *Biochim. Biophys. Acta.* 1550:6-19]. The crosslinking domains of tropoelastin contain lysine residues within proline-rich regions or polyalanine regions. The formation of covalent crosslinks of desmosine by lysyl oxidase action stabilizes the polymerized and insoluble product [Csiszar K. (2001) "*Lysyl oxidases: a novel multifunctional amine oxidase family*" *Prog. Nucleic Acid Res. Mol. Biol.* 70:1-32] and only two oxidase lysyl proteins, called LOX and LOXL, are capable of crosslinking insoluble elastin [Borel A., Eichenberger D., Farjanel J., Kessler. E., Gleyzal C., Hulmes D. J. S., Sommer P. and Font B. (2001) "*Lysyl oxidase-like protein from bovine aorta*" *J. Biol. Chem.* 276:48944-48949]. Additionally, the translated sequence of tropoelastin has a negatively charged hydrophilic C-terminal domain which is highly conserved between species. The major post-translational modifications that affect this molecule are hydroxylations of proline residues.

Elastogenesis is the process which leads to the generation of functional elastin in elastic fibers. It begins within the cell with the synthesis of the tropoelastin molecule, to which a galactose lectin of 67 kDa is added, which acts as a chaperone preventing the intracellular aggregation of tropoelastin molecules. The complex is secreted into the extracellular space, where galactose lectin interacts with the galactosugar of the microfibrils, thereby reducing its affinity for tropoelastin, which is locally released. The galactose lectin of 67 kDa is recycled and may resume its function, whereas tropoelastin is deposited in the skeleton formed by microfibrillar components through the interaction of the N-terminal domain of microfibril-associated glycoprotein (MAGP) with the C-terminal domain of tropoelastin. Once aligned, the majority of lysine residues of tropoelastin are deaminated and oxidized to aldehydes by the action of the $Cu^{2+}$-dependent lysyl oxidase. Crosslinking occurs throughout the reaction of said formed aldehydes with themselves or with unmodified lysine, and consequently tropoelastin chains become insoluble and the elastin network grows. Molecules belonging to the emiline and fibulin families, which are believed to possibly modulate the deposition of tropoelastin on microfibrils, are found in cell membrane-elastic fiber and elastin-microfibril interfaces. There is presently no evidence that molecules other than fibrillin are indispensable for the assembly of microfibrils [Kielty C. M., Sherratt M. J. and Shuttleworth C. A. (2002) "*Elastic fibers*" *J. Cell. Sci.* 115:2817-2828]. Mature elastin is an insoluble polymer of tropoelastins covalently joined by crosslinks, which may be bi-, tri- or tetrafunctional. It is believed that the complexity increases over time. The hydrophobic fragments are highly mobile and heavily contribute to the entropy of the system, and the amount of water hydrating the polymer in vivo also contributes to the entropy of the system [Debelle L. and Tamburro A. M. (1999) "*Elastin: molecular description and function*" Int. J. Biochem. Cell. Biol. 31:261-272].

Elastic fibers are important for maintaining skin elasticity, but also in other tissues and organs, like lungs or large blood vessel walls [Faury G. (2001) "*Function-structure relationship of elastic arteries in evolution: from microfibrils to elastin and elastic fibers*" Pathol. Biol. (Paris) 49:310-325]. Defects in the formation of elastic fibers, such as mutations in the genes that encode the different proteins which compose them, result in different pathologies. Thus, mutations in the fibrillin-1 gene are responsible for the Marfan syndrome (associated with skeletal, ocular and cardiovascular symptoms); mutations in the fibrillin-2 gene lead to congenital contractural arachnodactyly in addition to ocular and skeletal symptoms, and mutations in the elastin gene are the cause of the Williams syndrome, supravalvular stenosis and cutis laxa [Tassabehji M., Metcalfe K., Hurst J., Ashcroft G. S., Kielty C., Wilmot C., Donnai D., Read A. P. and Jones C. J. (1998) "*An elastin gene mutation producing abnormal tropoelastin and abnormal elastic fibers in a patient with autosomal dominant cutis laxa*" Hum. Mol. Genet. 6:1021-1028].

Elastic fibers have the purpose of maintaining flexibility throughout the life of a person. However, there are enzymes that may degrade them, resulting in loss of skin elasticity, which is a factor that significantly contributes to the aging of connective tissues and plays an important role in the degeneration of the skin by sun exposure [Watson R. E. B. Griffiths C. E. M., Craven N. M., Shuttleworth C. A. and Kielty C. M. (1999) "*Fibrillin-rich microfibrils are reduced in photoaged skin. Distribution at the dermal-epidermal junction*" J. Invest. Dermatol. 112:782-787].

Elastase is an enzyme that belongs to the family of serine proteases, which has carbohydrates attached to its surface. Its biological function is the degradation of elastin to allow neutrophil migration through connective tissues, so that they can destroy pathogenic microorganisms in case of infection. In humans, there are two genes that encode elastase, the pancreatic elastase gene and the neutrophil elastase gene, and elastase is produced and secreted by cells such as neutrophils, macrophages, fibroblasts and pancreatic cells. Other forms of elastase are found in microorganisms and in the venom of some snakes. The action of elastase may involve a decrease in the elasticity, health and quality of the skin. Several disorders have been described in which elastase activity is the direct or indirect cause of skin symptoms associated to it, such as wrinkles and stretch marks due to aging and photoaging, bullous pemphigoid, dermatitis and psoriasis. Elastase activity is also related with wound healing disorders such as keloids and hypertrophic scars, and skin alterations resulting from its lack of elasticity, like orange peel skin in cases of cellulite. Elastic fibers, due to their low rate of remodeling, appear at sites of trauma after some time, i.e. are absent in recent scars and their arrangement is abnormal in mature scars.

Collagens are the main family of fibrous proteins of the extracellular matrix, constituting 25% of the total proteic mass in mammals. They have been classified in more than 20 families, all of them having individual characteristics which fulfill specific functions in different tissues.

The main characteristic of collagen is its helicoidal structure formed by the association of three polypeptide chains rich in glycine and proline. Alterations in its amino acid composition cause dysfunction and loss of its mechanical properties [Culav E. M., Clark C. H. and Merrilees M. J. (1999) "*Connective tissues: matrix composition and its relevance to physical therapy*" Phys. Ther. 79:308-319]. These polypeptide chains can associate one to the other and form fibrils, which have a diameter of 10-300 nm and a length of up to hundreds of micrometers in mature tissues. These fibrils are often added into major structures, such as cable bunching, which can be seen through electronic microscopy as collagen fibers of several micrometers in diameter. This process is known as fibrillogenesis [Aumailley M. and Gayraud B. (1998) "*Structure and biological activity of the extracellular matrix*" J. Mol. Med. 76:253-265]. Not all collagens have the ability to form fibrils; only I, II, III, V and XI type collagens, which are known as fibrillar collagens.

An adult dermis is basically formed by fibrillar collagens type I, III and V. Type I collagen represents 80-90% of the total collagen of the dermis. Generally, type I collagen fibers feature a bigger diameter, which correlates with its ability to withstand a bigger mechanical load. Type III collagen intervenes in tissue extensibility, and with aging, it is replaced by type I collagen molecules, a process which is partly responsible for mature skins being less extensible than young skins. Type V collagen associates with types I and III regulating the diameter of fibrils ["*The Biology of the Skin*", Freinkel R. K. and Woodley D. T., eds. The Parthenon Publishing Group, 2001; Culav E. M., Clark C. H. and Merrilees M. J. (1999) "*Connective tissues: matrix composition and its relevance to physical therapy*" Phys. Ther. 79:308-319].

Collagen fibers are in constant renewal process, but such renewal decreases with age, causing the thinning of dermis. In addition, even though collagen fibers organization provides collagen network with great resistance, collagen fibers are sensitive to certain enzymes known as matrix metalloproteases (MMP). MMPs belong to a family of proteolytic enzymes (endoproteases) which contain a zinc atom coordinated with three cysteine residues and one residue of methionine in its active center and which can, collectively, degrade macromolecular components from the extracellular matrix and from the basal laminas into a neutral pH (collagen, elastin, etc.).

The solidity of the dermis is mainly due to the overlapping of the collagen fibers packed against each other in all directions. The collagen fibers contribute towards the elasticity and tonicity of the skin and/or mucous membranes. However, the thinning of the dermis is due not only to chronological aging but also to pathological causes such as, for example, the hypersecretion of corticoid hormones, certain diseases (Marfan's syndrome, Ehlers-Danlos syndrome) or vitamin deficiencies (scurvy). It is also accepted that extrinsic factors such as ultraviolet radiation, tobacco or certain treatments such as retinoic acid and derivatives, glucocorticoids or vitamin D and derivatives, also have an effect on the skin, mucous membranes and/or scalp and on its level of collagen. Degradation of the collagen fibers results in the appearance of loose, wrinkled skin, particularly on those skin areas exposed to the solar light such as the face, ears, neck, scalp, arms and hands, which people have always tried to combat, since skin which looks smooth and taut is preferred.

Skin damage associated to chronic exposition (repetitive irradiation) or high exposition (strong irradiation) to UVA and/or UVB rays has been studied; particularly it is known that UVB rays (290-300 nm; 5% of total UV rays) with more energetic wavelength especially affect epidermic cells (keratinocytes) acting over its DNA, and that UVA rays (320-400 nm; 95% of total UV rays) have a stronger penetration grade and also act over dermic cells such as fibroblasts and they act indirectly generating free radicals.

Moreover, prolonged exposure to UV radiation, particularly to UVA and/or UVB radiation stimulates MMP expression which destroy collagen [Fisher G. J., Datta S. C., Talwar H. S., Wang Z. Q., Varani J., Kang S, and Voorhees J. J. (1996) "*Molecular basis of sun-induced premature skin ageing and retinoid antagonism*" Nature 379:335-339; Fisher G. J., Wang Z. Q., Datta S. C., Varani J., Kang S, and Voorhees J. J. (1997) "*Pathophysiology of Prematur Skin Aging Induced by Ultraviolet Light*" New Eng. J. Med. 337:14191429; Fisher G. J., Choi H. C., Bata-Csorgo Z., Shao Y., Datta S., Wang Z. Q., Kang S, and Voorhees J. J. (2001) "*Ultraviolet irradiation increases matrix metalloproteinase-8 protein in human skin in vivo*" J. Invest. Dermatol. 117:219-226], especially matrix metalloelastase type 1 (MMP-1). This is one of the components of photoinduced skin aging or photoaging [Rittie L. and Fisher G. J. (2002) "*UV-light-induced signal cascades and skin aging*" Ageing Res. Rev. 1:705-720]. Besides, it is known that MMP-1, MMP-2 and MMP-9 activity increases with age and that this increase, together with cell growth deceleration, contributes to chronologic skin aging [EP 1 005 333 81]. Similarly, smokers' skin also has a premature aging aspect in which MMPs are overexpressed [Lahmann C., Bergemann J., Harrison G. and Young A. R. (2001) "*Matrix metalloproteinase-1 and skin aging in smokers*" Lancet 357:935-936].

Elastic fibers increase their crosslinks with time, decreasing the general elasticity and in parallel the progressive fragmentation of elastin causes a reduction of dermis density. These changes involve a loss of skin elasticity and the appearance of the hallmarks of aging. Moreover, the damage of the extracellular matrix induced by UV light leads to the appearance of wrinkles, loss of skin resilience and to actinic elastosis. Elastosis macroscopically appears as frequent yellowish nodules on the exposed skin. At the histological level, elastosis means an accumulation of basophilic amorphous material in the papillary dermis composed of elastin, microfibril proteins, fibronectin and type I and III collagen.

The clearest sign of aging is the appearance of wrinkles, which partially is due to the loss of skin elasticity. At the molecular level, elastic fibers have a linear appearance in young skin, which is indicative of elasticity. Crooked or curly fibers imply a lack of elasticity and are associated with age [Imokawa G., Takema Y, Yorimoto Y., Tsukahara K., Kawai M. and Imayama S. (1995) "*Degree of UV-induced tortuosity of elastic fibers in rat skin is age dependent*" J. Invest. Dermatol. 105:254-258]. The repair of skin wrinkling induced by agents such as trans-retinoic acid or $CO_2$ laser involves a recovery of the linearity of the elastic fibers [Tsukahara K., Takema Y., Moriwaki S., Fujimura T., Imayama S, and Imokawa G. (2001) "*Carbon dioxide laser treatment promotes repair of the three-dimensional network of elastic fibers in rat skin*" Br. J. Dermatol. 144:452-458, Tsukahara K., Takema Y, Fujimura T., Moriwaki S., Kitahara T., Imayama S, and Imokawa G. (1999) "*All-trans retinoic acid promotes the repair of tortuosity of elastic fibers in rat skin*" Br. J. Dermatol. 140:1048-1053]. The loss of linearity of elastic fibers may be due to secretion of elastase by surrounding fibroblasts, and may be accompanied by the absence of endogenous elastase inhibitors. Moreover, ultraviolet B (UVB) radiation can cause that the fibroblasts stop maintaining tension on the elastic fibers, making them lose linearity, with the consequent loss of flexibility. It has been shown that specific inhibition of skin elastase inhibits wrinkles, delays the loss of skin elasticity and slows the degradation of the three-dimensional structure of elastic fibers [Tsukahara K., Takema Y, Moriwaki S., Tsuji N., Suzuki Y., Fujimura T. and Imokawa G. (2001) "*Selective inhibition of skin fibroblast elastase elicits a concentration-dependent prevention of ultraviolet B-induced wrinkle formation*" J. Invest. Dermatol. 117:671-677]. The inhibition of elastase activity by topical application, therefore, can reduce, prevent or delay symptoms of aging and photoaging such as wrinkles, marks and expression lines.

Moreover, during the menopause, the main changes relating to the dermis are a decrease in the level of collagen and in the thickness of the dermis. In menopausal women, this results in thinning of the skin and/or mucous membranes. Women thus experience a sensation of "dry skin" or of skin which feels tight and an increase in the level of surface wrinkles and fine lines is observed. The skin looks rough to the touch. Lastly, the skin is less supple. It is demonstrated that women lose 2.1% of their level of collagen per year after the menopause and that 30% is lost in the first five years after the menopause [Brincat M., Kabalan S., Studd J. W., Moniz C. F., de Trafford J. and Montgomery J. (1987) "*A study of the decrease of skin collagen content, skin thickness, and bone mass in the postmenopausal woman*" Obstet. Gynecol. 70:840-845].

Proteases play an important role in different skin, mucous membranes and/or scalp conditions and disorders in which there is a degradation and destruction of collagen and/or elastin [Kahari V. M. and Saarialho-Kere U. (1997) "*Matrix metalloproteinases in skin*" Exp. Dermatol. 6:199-213]. Among the different pathologies described in which there is a degradation of collagen due to the activity of proteases in connective tissue cells, we find chronic ulcer [Miyoshi H., Kanekura T., Aoki T. and Kanzaki T. (2005) "*Beneficial effects of tissue inhibitor of metalloproteinases-2 (TIMP-2) on chronic dermatitis*" J. Dermatol. 32:346-353], psoriasis [Flisiak I., Mysliwiec H. and Chodynicka B. (2005) "*Effect of psoriasis treatment on plasma concentrations of metalloproteinase-1 and tissue inhibitor of metalloproteinase-1*" J. Eur. Acad. Dermatol. Venereol. 9:418-421; Suomela S., Kariniemi A. L., Impola U., Karvonen S. L., Snellman E., Uurasmaa T., Peltonen J., Saarialho-Kere U. (2003) "*Matrix metalloproteinase-19 is expressed by keratinocytes in psoriasis*" Acta Derm. Venereol. 83:108-114], oral pathologies such as gingivitis and periodontitis [Reynolds J. J. and Meikle M. C. (1997) "*The functional balance of metalloproteinases and inhibitors in tissue degradation: relevance to oral pathologies*" J. R. Coll. Surg. Edinb. 42:154-160], skin cancer [Ntayi C., Hornebeck W. and Bernard P. (2004) "*Involvement of matrix metalloproteinases (MMPs) in cutaneous melanoma progression*" Pathol. Biol. (Paris) 52:154-159; Kerkela E. and Saarialho-Kere U. (2003) "*Matrix metalloproteinases in tumor progression: focus on basal and squamous cell skin cancer*" Exp. Dermatol. 12:109-125] and tumor invasion and metastasis [Sato H., Takino T. and Miyamori H. (2005) "*Roles of membrane-type matrix metalloproteinase-1 in tumor invasion and metastasis*" Cancer Sci. 96:212-217].

Proteases also play a key role in different physiological situations in which the extracellular matrix is degraded or reconstructed, such as the extracellular matrix proteolytic remodeling, including tissue morphogenesis during development, tissue repair and angiogenesis [Kahari V. M. and Saarialho-Kere U. (1997) "*Matrix metalloproteinases in skin*" Exp. Dermatol. 6:199-213]. In a particular way, MMPs have a crucial role in connective tissue remodeling [Abraham D., Ponticos M. and Nagase H. (2005) "*Connective tissue remodeling: cross-talk between endothelins and matrix metalloproteinases*" Curr. Vasc. Pharmacol. 3:369-379], for example collagen degradation by MMPs makes the skin look wrinkled and flaccid.

Another skin and/or scalp pathologies or disorders, associated to MMP overexpression or to an increase of MMP activity in the connective tissue is acne [Papakonstantinou E., Aletras A. J., Glass E., Tsogas P., Dionyssopoulos A., Adjaye J., Fimmel S., Gouvousis P., Herwig R., Lehrach H., Zouboulis C. C. and Karakiulakis G. (2005) "*Matrix metalloproteinases of epithelial origin in facial sebum of patients with acne and their regulation by isotretinoin*" *J. Invest. Dermatol.* 125:673-684]. It is described that skins affected by acne have high levels of MMP-1.

Fibroblasts are not the only type of cells secreting elastase, elastase produced by neutrophils also contributes to the appearance of skin disorders or even pathologies. Neutrophil elastase or HLE (Human Leukocyte Elastase) is a proinflammatory agent that is known to be capable of degrading various components of extracellular matrix such as elastin, type III and IV collagen, and proteoglycans. The activity of neutrophil elastase is increased in the surface of the diseased skin of patients with psoriasis, atopic dermatitis and allergic contact dermatitis [Wiedow O., Wiese F., Streit V., Kalm C. and Christophers E. (1992) "*Lesional elastase activity in psoriasis, contact dermatitis, and atopic dermatitis,*" *J. Invest. Dermatol.* 99:306-309], pathologies characterized by leukocyte infiltration of the skin. Leukocyte infiltration of the skin, moreover, is increased by UV light [Woodbury R. A., Kligman L. H., Woodbury M. J. and Kligman A. M. (1994) "*Rapid assay of the anti-inflammatory activity of topical corticosteroids by inhibition of a UVA-induced neutrophil infiltration in hairless mouse skin. I. The assay and its sensitivity* "*Acta Derm. Venereol.* 74:15-17]. Furthermore, elastin degradation by elastase generates elastin fragments that act as cytokines contributing to a chronic inflammatory state associated with aging [Antonicelli F., Bellon G., Debelle L. and Hornebeck W (2007) "*Elastin-elastase and inflamm-aging*" *Curr. Top. Dev. Biol.* 79:99-155].

Psoriasis is a chronic skin inflammation whose cause is unknown. Its appearance is related to an inflammatory response mediated by elements of the immune system. The most characteristic feature of this pathology is the appearance of hyperplastic keratinized lesions accompanied by lymphocytic infiltration. These lesions expand at the edges, where there is a greater proliferative activity. It has been shown that elastase induces keratinocyte proliferation [Rogalski C., Meyer-Hoffert U., Proksch E. and Wiedow O. (2002) "*Human leukocyte elastase induces keratinocyte proliferation in vitro and in vivo*" *J. Invest. Dermatol.* 118:49-54]. These data indicate that dermal formulations containing compounds that inhibit the elastase enzyme activity are an adequate approximation to alleviate the symptoms of affected skin that occur with inflammation and leukocyte infiltration together with increased levels of elastase, for example and not limited to, for the treatment of psoriasis, atopic dermatitis and allergic contact dermatitis. People with dermatitis, including contact dermatitis and atopic dermatitis, also have high levels of some MMPs [Herouy Y., Mellios P., Bandemir E., Dichmann S., Nockowski P., Schöpf E. and Norgauer J. (2001) "*Inflammation in stasis dermatitis upregulates MMP-1, MMP-2 and MMP-13 expression*" *J. Dermatol. Sci.* 25:198-205; Devillers A. C., van Toorenenbergen A. W., Klein Heerenbrink G. J., Muldert P. G. and Oranje A. P. (2007) "*Elevated levels of plasma matrix metalloproteinase-9 in patients with atopic dermatitis: a pilot study*" *Clin. Exp. Dermatol.* 32:311-313; Miyoshi H., Kanekura T., Aoki T. and Kanzaki T. (2005) "*Beneficial effects of tissue inhibitor of metalloproteinases-2 (TIMP-2) on chronic dermatitis*" *J. Dermatol.* 32:346-353]. "Dermatitis" is defined as those skin conditions, disorders or pathologies that cause inflammation, including contact dermatitis, atopic dermatitis, sensitive skin and eczema.

Likewise, rosacea is a skin and/or scalp pathology or disorder in which MMPs are also involved. Rosacea is characterized by an increase of angiogenesis and inflammation. Angiogenesis refers to the process of new blood vessels formation and it includes benign conditions such as rosacea and malignant processes such as cancer. Matrix degrading enzymes, present in tissue extracellular matrix facilitate angiogenesis since they allow new blood vessels to penetrate the matrix. MMPs represent a kind of enzymes involved in such processes [Sapadin A. N., Fleischmajer R. (2006) "*Tetracyclines: Nonantibiotic properties and their clinical implications*" *J. Am. Acad. Derm.* 54:258-265].

Another inflammatory skin disease is bullous pemphigoid, which causes blistering. It has been demonstrated that neutrophils are involved in the onset of skin lesions in bullous pemphigoid, and their action is mediated by elastase [Liu Z., Shapiro S. D., Zhou X., Twining S. S., Senior R. M., Giudice G. J., Fairley J. A. and Diaz L. A. (2000) "*A critical role for neutrophil elastase in experimental bullous pemphigoid*" *J. Clin. Invest.* 105:113-123], so a topical application of an elastase inhibitor is a potentially valid treatment for alleviating the skin symptoms of this ailment.

Inhibition of elastase has other effects on the skin that are described in the state of the art. U.S. Pat. No. 7,211,278, for example, describes the use of elastase inhibitors as adjuvants in cosmetic formulations in order to suppress hair growth, for applications such as hair removal.

It is also known that MMPs are involved in perifollicular matrix degradation, and thus, in hair loss. Specifically, cytokines and the epidermal growth factor stimulate MMP-9 production in the lower epithelial compartment of hair root, such mechanism controls capillary follicle involution observed in alopecia [Jarrousse F., Boisnic S., Branchet M. C., Beranger J. Y., Godeau G., Breton L., Bernard B. A. and Mahé Y. F. (2001) "*Identification of clustered cells in human hair follicle responsible for MMP-9 gelatinolytic activity: consequences for the regulation of hair growth*" *Int. J. Dermatol.* 40:385-3921 Thus, overexpressed MMP inhibition during alopecic processes could be effective in delaying, and even preventing, hair loss [EP 1 076 549 B1].

Also, MMP activity is related to scar formation in tissues containing collagen. "Scar formation" is defined as the formation of an abnormal morphological collagen structure due to previous injuries or due to the healing process of tissue containing collagen on the skin.

Healing processes consist of three stages: (1) inflammation, (2) tissue formation and (3) tissue remodeling. A necessary stage in the healing process is extracellular matrix degradation: in order for the cells to proliferate in the wounded area and regenerate it, it is necessary that the extracellular matrix be degradated. Such degradation is made through MMPs. Healing process stages are regulated by a balance between the different MMPs and it has been described that an excess of MMP activity causes chronic ulcers. For example, an overexpression of MMP-8 can be associated to the pathogenesis of leg chronic ulcers. Likewise, diabetic ulcers are characterized by a prolonged inflammation, decrease collagen synthesis and high MMP levels.

Scars have different causes (accidents, surgery, skin diseases, burns, acne, infections and accidents in general), but not all scars are the same. Different kinds of scars can be grouped in Flat and pale scars: formed as a result of the body's natural healing process.

Sunken scars: formed by skin attached to deeper structures, such as muscles, or due to loss of fat in internal tissues. These scars are recessed into the skin and are usually the result of an injury.

Hypertrophic scars: appear when the body produces an excess of collagen during the healing process. These scars elevate over the skin surface and contain irregularly organized collagen.

Keloid scars: formed as a result of an imbalance in the production of collagen during the healing process. These scars not only elevate over skin surface, but also they extend beyond the boundary of the original wound and can continue to grow indefinitely.

Acne scars: formed in skin affected by acne. The scar can be sunken or become a keloid. People who have had chicken pox can have similar scars.

Stretched scars: occur when the skin around a healing wound is put under tension during the healing process. Initially, the scar may appear normal but can widen and thin over a period of weeks or months. This can occur when the wound is close to a joint and is stretched during movement or it may be due to poor healing because of general ill health or malnutrition.

Stretch marks: develop when the skin is stretched rapidly, for example during pregnancy or the adolescent growth spurt.

Therefore, skin scar reduction is desirable both from the pathological point of view, as healing during fibrotic processes, and from the cosmetic point of view, as in the case of softening the aspect of scars caused by acne or stretch marks. Potential benefits of the inhibition of elastase in relation to scarring have also been described. Thus, there is a degradation of elastin in areas around scars caused by acne vulgaris [Dick G. F., Ashe B. M., Rodgers E. G., Diercks R. C. and Goltz R. W. (1976) "*Study of elastolytic activity of Propionibacterium acnes and Staphylococcus epidermis in acne vulgaris and in normal skin*" Acta Derm. Venereol. 56:279-282]. Therefore, an elastase inhibitor would be effective as an adjuvant in a formulation of topical application to prevent the appearance of scars in skin affected by acne. Moreover, U.S. Pat. No. 5,922,319 describes the application of an elastase inhibitor to prevent the formation of scars on the cornea in cases of eye trauma.

It has also been described that during adipocytes proliferation and differentiation, MMPs are overexpressed [Traurig M. T., Permana P. A., Nair S., Kobes S., Bogardus C. and Baier L. J. (2006) "*Differential expression of matrix metalloproteinase 3 (MMP3) in preadipocytes/stromal vascular cells from nonobese nondiabetic versus obese nondiabetic Pima Indians*" Diabetes 55:3160-3165]. Thus, the collagen network of the skin affected by cellulite is destroyed, which is one of the causes of the orange peel skin aspect. Therefore, supplementing the skin with compounds able to stimulate collagen synthesis will help to reduce such collagen destruction and become an effective anti-cellulite treatment. Inhibition of elastase also helps to alleviate the effects of collagen degradation, for example preventing the appearance of marks as a result of aging and improving skin irregularities such as the orange peel skin that is characteristic of cellulite.

MMP activity is also responsible for the extracellular matrix disorganization that surrounds lymphatic and blood vessels. Matrix deterioration around blood vessels allows for a passive vasodilatation which gives place to capillary visibility or telangiectasia, or couperosis. Besides, this microcapillary passive dilatation can cause local blood vessel bursts which can give place to bags under the eyes or dark circles in the periorbital area. Furthermore, MMPs have an influence over vein wall mechanical properties, which can make veins fragile and consequently lead to the development of varicose veins.

Apart from the relation of MMPs to tissue matrix degradation, it has been suggested that MMPs are also involved in different pathologies that concur with an abnormal metabolism of the connective tissue or basal membrane matrix such as arthritis (rheumatoid arthritis, osteoarthritis, etc), bone diseases (osteoporosis, etc.), ectopic angiogenesis, multiple sclerosis, tumors metastasis and tissue ulcers (cornea, stomach, epidermis, etc.) [EP 0 927 161 B1]. Therefore, an MMP inhibitor could be effective in treating and preventing those pathologies caused by an abnormal metabolism of the tissular matrix.

The importance of the presence of collagen and elastin fibers in the skin, mucous membranes and/or scalp and the importance of maintaining, or even reinforcing, their presence can thus be appreciated. It is thus important to have available products whose effects are directed towards maintaining the levels and integrity of collagen and/or elastin in the skin and maintaining the skin's smooth and taut appearance reducing, delaying and/or preventing the signs of aging and/or photoaging. Retaining an elevated elastin and/or collagen content in the skin or increasing the elastin and/or collagen content in the skin may be achieved in various different ways. On one hand, substances which inhibit matrix proteases may be used. On the other hand, however, it is also possible to use substances which increase collagen and/or elastin synthesis in order, by de novo synthesis, to counter the negative effects of such protease-induced collagen and/or elastin degradation. The reduction in de novo protein synthesis which accompanies increasing age may here be at least partially compensated by using active ingredients which increase collagen and/or elastin synthesis.

In the context of this invention the terms "aging" and "aging skin" are used to describe the emergence of visible changes in skin appearance as well as those perceptible by touch, such as for example and in a non-limiting sense wrinkles, fine lines, roughness, expression lines, stretch marks, discontinuities, furrows, flaccidity, skin sagging, such as cheeks sagging, eye pouches, double chin, increase of pore size, loss of elasticity, loss of resilience, loss of firmness, elastosis, anomalous differentiation, hyperkeratinization, keratosis, changes of the skin color, such as marks, reddening or bags under the eyes, appearance of hyperpigmented areas such as age spots, melasma or freckles, loss of smoothness, orange-peel skin, loss of collagen structure and other histological changes of the stratum corneum, of the dermis, epidermis, vascular system (for example the appearance of spider veins or telangiectasias) or of those tissues close to the skin. Skin aging is a process with two main components: chronological, which is due to the passage of time, and photo-induced, which is due to the level of exposure to ultraviolet (UV) radiation and which is known as photoaging. The sum of several environmental factors such as exposure to tobacco smoke, exposure to pollution, and climatic conditions like cold and/or wind also contribute to skin aging.

There are descriptions in the state of the art of various vegetable extracts with elastase inhibitory activity [e.g. JP 11-246386, JP 2000-072649, JP 11-279041, U.S. Pat. No. 6,395,261, U.S. Pat. No. 6,238,674], and synthetic chemical compounds with this activity [U.S. Pat. No. 4,643,991, U.S. Pat. No. 5,008,245, U.S. Pat. No. 5,162,307, U.S. Pat. No. 5,189,178]. Particularly, the U.S. Pat. No. 4,665,053 describes synthetic lipopeptides rich in alanine and proline, in particular lipopeptides containing the L-Ala-L-Ala dipeptide, as elastase inhibitors.

Individual substances which are frequently mentioned in connection with increasing collagen synthesis and are thus prior art are for example active ingredients such as ascorbic acid and the derivatives thereof such as in particular ascorbyl palmitate, magnesium ascorbyl phosphate, sodium ascorbyl phosphate and ascorbyl alpha- and beta-glucoside, retinol and derivatives of retinol such as retinoic acid, retinal, retinol, retinyl acetate or retinyl palmitate or vegetable extracts such as for example extracts of *Aloe* and *Centella* species. Active ingredients which are furthermore frequently used to stimulate collagen synthesis also include peptide substances and the derivatives thereof such as e.g. carnitine, carnosine, creatine, matrikine peptides (e.g. lysyl-threonyl-threonyl-lysyl-serine) and further peptide structures such as palmitoylated pentapeptides (e.g. Matrixyl® from Sederma/Croda) or the oligopeptide with the trade name Vincipeptide (from Vincience, France). Moreover, compounds such as asiatic acid, madecassic acid, madecassoside, asiaticoside, extracts of *Centella asiatica*, niacinamide, astaxanthine, glucans e.g. from yeasts and oats, soy extract and soy isoflavones, such as genistein and daidzein, rutin, chrysin, morin, betel nut alkaloids, forskolin, betulinic acid, extracts of *Plantago* species, TGF-beta, extracts of *Ginkgo biloba*, glutamine and glycolic acid are used as collagen synthesis stimulators.

This invention describes synthetic peptides containing uncoded amino acids effective in inhibiting elastase and/or stimulating collagen synthesis in the skin, mucous membranes and/or scalp. No peptide with uncoded amino acids in its sequence presenting elastase inhibitory activity and/or stimulating collagen synthesis in the skin, mucous membranes and/or scalp exists in the state of the art. The use of uncoded amino acids makes their recognition by proteases difficult, increasing the half-life of the peptides that contain them. This increase in the half-life of the peptide extends their efficacy in inhibiting elastase and/or stimulating collagen synthesis.

Hence, despite the large array of existing compounds and/or extracts with an activity against the enzymes that degrade either collagen or elastin or with a potential for estimulating the endogenous synthesis of either collagen or elastin in the skin, mucous membranes and/or scalp, there is still a need to identify new elastase inhibitors and/or collagen synthesis stimulators that are more effective and more selective than those known in the state of the art.

DETAILED DESCRIPTION OF THE INVENTION

This invention provides a solution to the problem mentioned hereinabove. Surprisingly, the applicant of this invention has found that certain synthetic peptides with uncoded amino acids have a significant efficacy in inhibiting elastase and/or stimulating collagen synthesis in the skin, mucous membranes and/or scalp and therefore are useful for the treatment, prevention and/or care of any conditions, disorders and/or diseases of the skin, mucous membranes and/or scalp that result from elastase activity and/or which benefit from stimulation of collagen synthesis.

Definitions

To facilitate the understanding of this invention, the meanings of some terms and expressions as used in the context of the invention are included.

In this description, the abbreviations used for amino acids follow the rules of the Commission on Biochemical Nomenclature of the IUPAC-IUB specified in *Eur. J. Biochem.* (1984) 138:9-37 and *J. Biol. Chem.* (1989) 264:633-673.

Thus, for example, Gly represents $NH_2$—$CH_2$—COOH, Gly- represents $NH_2$—$CH_2$—CO—, -Gly represents —NH—$CH_2$—COOH and -Gly- represents —NH—$CH_2$—CO—. Therefore, the hyphen, which represents the peptide bond, eliminates the OH from the 1-carboxyl group of the amino acid (represented here in the conventional non-ionized form) when placed to the right of the symbol, and eliminates the H from the 2-amino group of the amino acid when placed to the left of the symbol; both modifications can be applied to the same symbol (see Table 1).

TABLE 1

Structures of amino acids and their nomenclature in three-letter code

| Symbol | Residue |
|---|---|
| -Gly- | 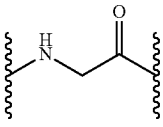 [SMILES: *NCC(*)=O] |
| -Arg- | 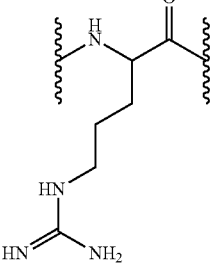 |
| -Trp- | 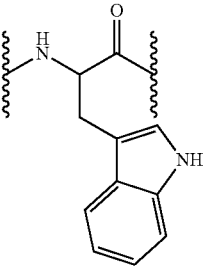 [SMILES: *NC(Cc1c[nH]c2ccccc12)C(*)=O] |
| -Ala- | 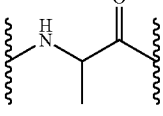 |
| -Cit- | 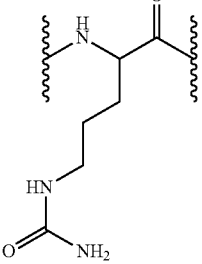 |

TABLE 1-continued

Structures of amino acids and their nomenclature in three-letter code

| Symbol | Residue |
|---|---|
| -Tyr- | (structure of tyrosine residue) |
| -Val- | (structure of valine residue) |
| -Nle- | (structure of norleucine residue) |
| -Phg- | (structure of phenylglycine residue) |

The abbreviation "Ac-" is used in this description to designate the acetyl group ($CH_3$—CO—) and the abbreviation "Palm-" is used to designate the palmitoyl group ($CH_3$—$(CH_2)_{14}$—CO—).

The term "non-cyclic aliphatic group" is used in this invention to encompass, for example and not limited to, linear or branched alkyl, alkenyl and alkynyl groups.

The term "alkyl group" refers to a linear or branched saturated group, which has between 1 and 24, preferably between 1 and 16, more preferably between 1 and 14, more preferably between 1 and 12, still more preferably 1, 2, 3, 4, 5 or 6 carbon atoms and is bound to the rest of the molecule through a single bond, including, for example and not limited to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a, linear or branched group, which has between 2 and 24, preferably between 2 and 16, more preferably between 2 and 14, more preferably between 2 and 12, still more preferably 2, 3, 4, 5 or 6 carbon atoms with one or more carbon-carbon double bonds, preferably with 1, 2 or 3 carbon-carbon double bonds, conjugated or unconjugated, which is bound to the rest of the molecule through a single bond, including, for example and not limited to, vinyl, oleyl, linoleyl group and similar.

The term "alkynyl group" refers to a linear or branched group, which has between 2 and 24, preferably between 2 and 16, more preferably between 2 and 14, more preferably between 2 and 12, still more preferably 2, 3, 4, 5 or 6 carbon atoms with one or more carbon-carbon triple bonds, preferably 1, 2 or 3 carbon-carbon triple bonds, conjugated or unconjugated, which is bound to the rest of the molecule through a single bond, including, for example and not limited to, the ethynyl, 1-propynyl, 2-propynyl, 1-butynyl, 2-butynyl, 3-butynyl, pentynyl group, such as 1-pentynyl, and similar.

The term "alicyclyl group" is used in this invention to encompass, for example and not limited to, cycloalkyl, cycloalkenyl and cycloalkynyl groups.

The term "cycloalkyl" refers to a saturated mono- or polycyclic aliphatic group which has between 3 and 24, preferably between 3 and 16, more preferably between 3 and 14, more preferably between 3 and 12, even more preferably 3, 4, 5 or 6 carbon atoms and is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, more preferably between 5 and 12, still more preferably 5 or 6 carbon atoms with one or more carbon-carbon double bonds, preferably 1, 2 or 3 carbon-carbon double bonds, conjugated or unconjugated, which is bound to the rest of the molecule through a single bond, including, for example and not limited to, the cyclopent-1-en-1-yl group and similar.

The term "cycloalkynyl" refers to a non-aromatic mono- or polycyclic aliphatic group which has between 5 and 24, preferably between 5 and 16, more preferably between 5 and 14, more preferably between 5 and 12, still more preferably 5 or 6 carbon atoms with one or more carbon-carbon double bonds, preferably 1, 2 or 3 carbon-carbon triple bonds, conjugated or unconjugated, which is bound to the rest of the molecule through a single bond, including, for example and not limited to, the cyclohex-1-yn-1-yl group and similar.

The term "aryl group" refers to an aromatic group which has between 6 and 30, preferably between 6 and 18, more preferably between 6 and 10, more preferably 6 or 10 carbon atoms, comprising 1, 2, 3 or 4 aromatic rings, bound through a carbon-carbon or fused, including, for example and not limited to, phenyl, naphthyl, diphenyl, indenyl, phenanthryl or anthranilic among others; or to an aralkyl group.

The term "aralkyl group" refers to an alkyl group substituted with an aromatic group which has between 7 and 24 carbon atoms and includes, for example and not limited to, —$(CH_2)_{1-6}$-phenyl, —$(CH_2)_{1-6}$-(1-naphtyl), —$(CH_2)_{1-6}$-(2-naphtyl), —$(CH_2)_{1-6}$—CH(phenyl)$_2$ and similar.

The term "heterocyclyl group" refers to a hydrocarbon ring with 3-10 members, in which one or more atoms of the ring, preferably 1, 2 or 3 atoms of the ring, are an element other than carbon, for example nitrogen, oxygen or sulfur, and may be saturated or unsaturated. For the purposes of this invention, the heterocycle may be monocyclic, bicyclic or tricyclic ring system, which may include fused ring systems; atoms of nitrogen, carbon or sulfur may optionally be oxidized in the heterocyclyl radical; the nitrogen atom can be optionally quaternized; and the heterocyclyl radical may be partially or completely saturated or be aromatic. With increasing preference, the term heterocyclyl refers to a ring with 5 or 6 members.

The term "heteroarylalkyl group" refers to an alkyl group substituted with a substituted or unsubstituted aromatic heterocyclyl group, the alkyl group having between 1 and 6 carbon atoms and the aromatic heterocyclyl group between 2 and 24 carbon atoms and 1 to 3 atoms other than carbon, including, for example and not limited to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As used in this technical area, there may be a degree of substitution on the groups defined above. Thus, there can be substitution in any of the groups of this invention. The references herein to substituted groups in the groups of this invention indicate that the specified radical may be substituted in one or more available positions by one or more substituents, preferably in 1, 2 or 3 positions, more preferably within 1 or 2 positions, still more preferably in 1 position. These substituents include, for example and not limited to, $C_1$-$C_4$ alkyl; hydroxyl; $C_1$-$C_4$ alkoxy; amino; $C_1$-$C_4$ aminoalkyl; $C_1$-$C_4$ carbonyloxyl; $C_1$-$C_4$ oxycarbonyl; halogen such as fluorine, chlorine, bromine and iodine; cyano; nitro; azido; $C_1$-$C_4$ alkylsulfonyl; thiol; $C_1$-$C_4$ alkylthio; aryloxyl such as phenoxyl; —$NR_b(C=NR_b)NR_bR_c$, wherein $R_b$ and $R_c$ are independently selected from the group consisting of H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, 3-10 member heterocyclyl or a protecting group of the amino group.

Compounds of the Invention

The compounds of the invention are defined by the general formula (I)

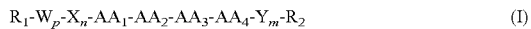

$$R_1\text{-}W_p\text{-}X_n\text{-}AA_1\text{-}AA_2\text{-}AA_3\text{-}AA_4\text{-}Y_m\text{-}R_2 \quad (I)$$

their stereoisomers, mixtures thereof and/or their cosmetically or pharmaceutically acceptable salts, characterized in that at least one of the amino acids $AA_1$, $AA_2$ or $AA_4$ is uncoded and:

$AA_1$ is selected from the group consisting of -Arg-, -Phg- and -Nle- or is a bond;

$AA_2$ is selected from the group consisting of -Ala-, -Phg-, -Cit- and -Nle-;

$AA_3$ is selected from the group consisting of -Trp-, -Val- and -Tyr-;

$AA_4$ is selected from the group consisting of -Phg- and -Gly-;

W, X and Y are independently selected from the group consisting of coded or uncoded amino acids;

p, n and m range between 0 and 1;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—;

$R_2$ is selected from the group consisting of —$NR_3R_4$, —$OR_3$ and —$SR_3$;

wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl and substituted or unsubstituted aralkyl;

wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

and provided that when $AA_1$ is a bond, $AA_2$ is -Phg- and $AA_3$ is -Trp-.

$R_1$ and $R_2$ groups are bound to the amino-terminal (N-terminal) and carboxy-terminal (C-terminal) of the peptide sequences respectively.

According to a preferred embodiment of this invention, $R_1$ is selected from the group consisting of H and $R_5$—CO—, wherein $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl with 2 to 24 carbon atoms and 1 to 3 atoms other than carbon and an alkyl chain of 1 to 6 carbon atoms. More preferably, $R_1$ is selected from H, acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl. Even more preferably, $R_1$ is H, acetyl, lauroyl, palmitoyl or miristoyl. In an even more preferred embodiment, the radical $R_1$ is acetyl.

According to another preferred embodiment, $R_2$ is —$NR_3R_4$, —$OR_3$ or —$SR_3$, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl with 2 to 24 carbon atoms and 1 to 3 atoms other than carbon and an alkyl chain of 1 to 6 carbon atoms. Optionally, $R_3$ y $R_4$ can be bound through a carbon-carbon bond, saturated or unsaturated, forming a cycle with the nitrogen atom. More preferably, $R_2$ is —$NR_3R_4$ or —$OR_3$, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl with 3-10 ring members, and substituted or unsubstituted heteroarylalkyl with 3 to 10 members and an alkyl chain with 1 to 6 carbon atoms. More preferably $R_3$ and $R_4$ are selected from the group consisting of H, methyl, ethyl, hexyl, dodecyl or hexadecyl. Even more preferably $R_3$ is H and $R_4$ is selected from the group consisting of H, methyl, ethyl, hexyl, dodecyl or hexadecyl. According to a more preferred embodiment, $R_2$ is selected from —OH and —$NH_2$.

According to another embodiment of the invention $AA_2$ is -Phg- and $AA_4$ is -Phg-.

According to another embodiment of this invention, $R_1$ is selected from the group consisting of H, acetyl, lauroyl, miristoyl or palmitoyl, $AA_1$ is -L-Arg-, $AA_2$ is -L-Phg- or -D-Phg-, $AA_3$ is -L-Tyr-, $AA_4$ is -L-Phg- or -D-Phg- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl and $R_2$ is —OH. Even more preferably, p, n and m are 0.

According to another embodiment of this invention, $R_1$ is selected from the group consisting of H, acetyl, lauroyl, miristoyl or palmitoyl, $AA_1$ is -L-Nle-, $AA_2$ is -L-Phg- or -D-Phg-, $AA_3$ is -L-Tyr-, $AA_4$ is -L-Phg- or -D-Phg- and $R_2$ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is -L-Arg-, AA₂ is -L-Phg- or -D-Phg-, AA₃ is -L-Trp-, AA₄ is -L-Phg- or -D-Phg- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is -L-Nle-, AA₂ is -L-Phg- or -D-Phg-, AA₃ is -L-Trp-, AA₄ is -L-Phg- or -D-Phg- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is -L-Arg-, AA₂ is -L-Phg- or -D-Phg-, AA₃ is -L-Val-, AA₄ is -L-Phg- or -D-Phg- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is -L-Arg-, AA₂ is -L-Phg- or -D-Phg-, AA₃ is -L-Val-, AA₄ is -Gly- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is -L-Phg- or -D-Phg-, AA₂ is -L-Phg- or -D-Phg-, AA₃ is -L-Trp-, AA₄ is -L-Phg- or -D-Phg- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl or palmitoyl, AA₁ is a bond, AA₂ is -L-Phg- or -D-Phg-, AA₃ is -L-Trp-, AA₄ is -L-Phg- or -D-Phg- and R₂ is —NR₃R₄ or —OR₃ wherein R₃ and R₄ are independently selected from H, methyl, ethyl, hexyl, dodecyl and hexadecyl, preferably R₂ is —OH or —NH₂. More preferably, R₁ is acetyl and R₂ is —OH. Even more preferably, p, n and m are 0.

According to another embodiment of this invention, R₁ is selected from the group consisting of H, acetyl, lauroyl, miristoyl and palmitoyl, preferably R₁ is selected from the group consisting of H, acetyl and palmitoyl and preferably R₂ is selected from the group consisting of —OH and —NH₂.

Preferably, the compounds of formula (I) are selected from the group consisting of:

```
Ac-Arg-Phg-Val-Gly-OH;
Ac-Arg-Phg-Val-Gly-NH₂,
Ac-Arg-Phg-Val-Phg-OH,
Ac-Arg-Phg-Val-Phg-NH₂,
Ac-Arg-Phg-Trp-Phg-OH,
Ac-Arg-Phg-Trp-Phg-NH₂,
Ac-Nle-Phg-Trp-Phg-OH,
Ac-Nle-Phg-Trp-Phg-NH₂,
Ac-Phg-Phg-Trp-Phg-OH,
Ac-Phg-Phg-Trp-Phg-NH₂,
Ac-Phg-Phg-Val-Phg-OH,
Ac-Phg-Phg-Val-Phg-NH₂,
Ac-Phg-Phg-Val-Gly-OH,
Ac-Phg-Phg-Val-Gly-NH₂,
Ac-Nle-Phg-Val-Phg-OH,
Ac-Nle-Phg-Val-Phg-NH₂,
Ac-Phg-Phg-Tyr-Phg-OH,
Ac-Phg-Phg-Tyr-Phg-NH₂,
Ac-Nle-Phg-Tyr-Phg-OH,
Ac-Nle-Phg-Tyr-Phg-NH₂,
Ac-Arg-Phg-Tyr-Phg-OH,
Ac-Arg-Phg-Tyr-Phg-NH₂,
Ac-Nle-Ala-Trp-Phg-OH,
Ac-Nle-Ala-Trp-Phg-NH₂,
Ac-Nle-Ala-Tyr-Phg-OH,
Ac-Nle-Ala-Tyr-Phg-NH₂,
Ac-Nle-Phg-Tyr-Gly-OH,
Ac-Nle-Phg-Tyr-Gly-NH₂,
Palm-Phg-Cit-Trp-Phg-OH,
Palm-Phg-Nle-Trp-Phg-NH₂,
H-Arg-Cit-Val-Phg-OH,
H-Arg-Nle-Val-Phg-OH,
Ac-Arg-Nle-Val-Gly-OH,
Ac-Arg-Nle-Val-Gly-NH₂,
Ac-Phg-Trp-Phg-OH,
Ac-Phg-Trp-Phg-NH₂,
Palm-Arg-Phg-Val-Phg-NH₂,
Palm-Arg-Phg-Trp-Phg-NH₂,
Ac-Arg-Phg-Trp-Phg-NH—(CH₂)₁₅—CH₃,
H-Arg-Phg-Val-Gly-NH₂
Ac-Phg-Phg-Trp-Phg-OH,
```

```
Ac-Phg-Phg-Trp-Gly-OH,

Ac-Nle-Phg-Val-Gly-OH,

Ac-Nle-Phg-Trp-Gly-OH,

Ac-Gly-Phg-Phg-Trp-Phg-Gly-OH,

Ac-Ala-Gly-Nle-Phg-Trp-Phg-OH,

Ac-Gly-Gly-Arg-Phg-Trp-Phg-Gly-OH,

Ac-Arg-Phg-Tyr-Phg-Ile-OH,

Ac-Leu-Nle-Phg-Tyr-Phg-Gly-NH_2,

Ac-Ser-Phe-Arg-Phg-Val-Phg-Phg-OH,
and

Ac-Phg-Phg-Arg-Phg-Val-Gly-Phg-OH;
``` their stereoisomers, mixtures thereof and/or their cosmetically or pharmaceutically acceptable salts.

The peptides of this invention can exist as stereoisomers or mixtures of stereoisomers, for example, the amino acids that forming them can have L-, D-configuration, or be racemic independently of one another. It is therefore possible to obtain isomeric mixtures as well as racemic mixtures or diastereomeric mixtures, or pure diastereomers or enantiomers, depending on the number of asymmetric carbons and which isomers or isomeric mixtures are present. The preferred structures of the peptides of the invention are pure isomers, i.e., enantiomers or diastereomers.

For example, when it is indicated that $AA_1$ can be -Phg-, it is understood that $AA_1$ is selected from -L-Phg-, -D-Phg- or mixtures of both, racemic or non-racemic. Equally, when it is said that $AA_2$ can be -Arg-, it is understood that it can be -L-Arg-, -D-Arg- or mixtures of both, racemic or non-racemic. The preparation processes described herein allow the person skilled in the art to obtain each of the stereoisomers of the peptides of the invention by choosing the amino acid with the appropriate configuration.

In the context of this invention, the term "uncoded amino acids" refers to those amino acids not coded by the genetic code, natural or not, for example and not limited to, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isopipecotic acid, isoserine, phenylglycine, statin, β-alanine, norleucine, N-methyl amino acids, β-amino acids or γ-amino acids among others, and their derivatives. A list of unnatural amino acids can be found in the article "Unusual amino acids in peptide synthesis" by D. C. Roberts and F. Vellaccio, in The Peptides, Vol 5 (1983), Chapter VI, Gross E. and Meienhofer J., Academic Press, New York, USA or in the trade catalogs of specialized companies such as NeoMPS, Bachem, Novabiochem, Sigma-Aldrich, Peptides International, Advanced ChemTech, Chem-Impex, Maybridge Chemical Technology Chirotech, Peninsula Laboratories or RSP Amino Acid Analogues, among others.

In the context of this invention, when p, n and m are other than 0, it is clearly understood that the nature of W, X and Y does not hinder the activity of the peptides of the invention, but rather contributes to the inhibition of elastase and/or stimulates the collagen synthesis or has no effect on them.

The scope of this invention also includes cosmetically or pharmaceutically acceptable salts of the peptides provided by this invention. The term "cosmetically or pharmaceutically acceptable salts" means a salt admitted for its use in animals and more particularly in humans, and includes the salts used to form base addition salts, either inorganic, such as and not limited to, lithium, sodium, potassium, calcium, magnesium, manganese, copper, zinc or aluminum, among others, or organic such as and not limited to, ethylamine, diethylamine, ethylenediamine, ethanolamine, diethanolamine, arginine, lysine, histidine or piperazine among others, or acid addition salts, either organic, for example and not limited to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not limited to, chloride, sulfate, borate or carbonate among others. The nature of the salt is not critical, provided it is cosmetically or pharmaceutically acceptable. The cosmetically or pharmaceutically acceptable salts of the peptides of the invention can be obtained by conventional methods well known in the state of the art [S. M. Berge, L. D. Bighley and Monkhouse D. C. (1977) "*Pharmaceutical Salts*" *J. Pharm. Sci* 66:1-19].

Another aspect of this invention refers to a peptide of general formula (I), its stereoisomers, mixtures thereof and/or its cosmetically or pharmaceutically acceptable salts, as described in this invention, for the treatment and/or care of skin, mucous membranes and/or scalp.

In one particular aspect, this invention relates to a peptide of general formula (I), its stereoisomers, mixtures thereof, and/or its cosmetically or pharmaceutically acceptable salts, as described in this invention, for the treatment, prevention and/or care of those conditions, disorders and/or diseases of the skin, mucous membranes and/or scalp which are the result of elastase activity.

In another particular aspect, this invention relates to a peptide of general formula (I), its stereoisomers, mixtures thereof, and/or its cosmetically or pharmaceutically acceptable salts, as described in this invention, for the treatment, prevention and/or care of those conditions, disorders and/or diseases of the skin, mucous membranes and/or scalp which benefit from stimulation of collagen synthesis.

In another particular aspect, this invention relates to a peptide of general formula (I), its stereoisomers, mixtures thereof, and/or its cosmetically or pharmaceutically acceptable salts, as described in this invention, for inhibition of elastase, preferably, for inhibition of elastase in the skin, mucous membranes and/or scalp.

In another particular aspect, this invention relates to a peptide of general formula (I), its stereoisomers, mixtures thereof, and/or its cosmetically or pharmaceutically acceptable salts, as described in this invention, for stimulation of collagen synthesis, preferably, for stimulation of collagen synthesis in the skin, mucous membranes and/or scalp.

In another particular aspect, this invention relates to a peptide of general formula (I), its stereoisomers, mixtures thereof, and/or its cosmetically or pharmaceutically acceptable salts, as described in this invention, which increases elasticity of the skin, mucous membranes and/or scalp.

In another particular aspect, this invention relates to a peptide of general formula (I), its stereoisomers, mixtures thereof, and/or its cosmetically or pharmaceutically acceptable salts, as described in this invention, which reduces or eliminates facial wrinkles.

In another particular aspect, this invention relates to a peptide of general formula (I), its stereoisomers, mixtures thereof, and/or its cosmetically or pharmaceutically acceptable salts, as described in this invention, for treatment and/or care of the skin and/or scalp, which reduces, delays and/or prevents the signs of aging and/or photoaging.

In another particular aspect, this invention relates to a peptide of general formula (I), its stereoisomers, mixtures thereof, and/or its cosmetically or pharmaceutically acceptable salts, as described in this invention, for treatment and/or care of the skin, mucous membranes and/or scalp affected by wrinkles, expression wrinkles, stretch marks, skin aging, skin photoaging, wound healing disorders, ulcers, diabetic ulcers, keloids, hypertrophic scars, acne, cellulite, orange peel skin, elastosis, actinic elastosis, keratosis, inflammation, dermatitis, atopic dermatitis, allergic contact dermatitis, sensitive skin, eczema, bullous pemphigoid, gingivitis, periodontitis, skin cancer, tumor invasions, tumour metastasis, telangiectasia, couperosis, varicose veins, eye dark circles, bags under the eye, alopecia and hair loss, rosacea and/or psoriasis.

In another particular aspect, this invention relates to a peptide of general formula (I), its stereoisomers, mixtures thereof, and/or its cosmetically or pharmaceutically acceptable salts, as described in this invention, for hair treatment or hair hygiene.

In another particular aspect, this invention relates to a peptide of general formula (I), its stereoisomers, mixtures thereof, and/or its cosmetically or pharmaceutically acceptable salts, as described in this invention, for treatment and/or care of skin of the face and/or body or facial and/or bodily hygiene.

In another particular aspect, the treatment, prevention and/or care of this invention is performed by topical or transdermal application; preferably, the topical or transdermal application is performed via iontophoresis, sonophoresis, electroporation, mechanical pressure, osmotic gradient pressure, occlusive cure, microinjections, needle-free injections by means of pressure, by means of microelectric patches or any combination thereof.

In another particular aspect, the treatment, prevention and/or care is done by oral administration.

Procedures for Preparation

The synthesis of the peptides of the invention, their stereoisomers, mixtures thereof, and/or their cosmetically or pharmaceutically acceptable salts can be performed according to conventional methods known in the prior art, such as for example, methods of solid phase peptide synthesis [Stewart J. M. and Young J. D. (1984) "*Solid Phase Peptide Synthesis, 2nd edition*" Pierce Chemical Company, Rockford, Ill.; Bodanzsky M. and Bodanzsky A. (1984) "*The practice of Peptide Synthesis*" Springer Verlag, New York, Lloyd Williams P., Albericio F. and Giralt E. (1997) "*Chemical Approaches to the Synthesis of Peptides and Proteins*" CRC, Boca Raton, Fla., USA], methods of synthesis in solution, a combination of methods for solid phase synthesis and solution synthesis, or methods of enzymatic synthesis [Kullmann W. (1980) "*Proteases as catalysts for enzymic syntheses of opioid peptides*" *J. Biol. Chem.* 255:8234-8238]. The peptides can also be obtained by fermentation of a bacterial strain, genetically engineered or not, in order to produce the desired sequences, or by controlled hydrolysis of proteins of animal or vegetable origin, preferably vegetable origin, to release peptide fragments containing at least the desired sequence.

For example, a method for obtaining the peptides of the invention of formula (I) comprises the steps of:

coupling an amino acid with the N-terminal end protected and the C-terminal end free, onto an amino acid with the N-terminal end free and the C-terminal end protected or bound to a solid support;

removing the protecting group of the N-terminal end;

repeating of the sequence of coupling and removing the protecting group of the N-terminal to obtain the desired peptide sequence;

removing the protecting group of the C-terminal end or cleaving from the solid support.

Preferably, the C-terminal end is bound to a solid support and the process is conducted on solid phase and therefore includes the coupling of an amino acid with the N-terminal end protected and the C-terminal end free onto an amino acid with the N-terminal end free and the C-terminal end bound to a polymer support, removal of the protecting group of the N-terminal end; and repetition of this sequence as many times as necessary to obtain a tetrapeptide, and finally followed by cleaving the synthesized peptide from the original polymer support.

The functional groups of the side chains of amino acids remain adequately protected with temporary or permanent protecting groups throughout the synthesis and can be deprotected simultaneously or orthogonally to the process of cleaving the peptide from the polymer support.

Alternatively, the solid phase synthesis can be carried out by a convergent strategy coupling a dipeptide or a tripeptide onto the polymer support or onto a dipeptide or amino acid previously bound to the polymer support. Convergent synthesis strategies are widely known by the person skilled in the art and are described in Lloyd-Williams P., Albericio F. and Giralt E. on "*Convergent solid phase peptide synthesis*" (1993) *Tetrahedron* 49:11065-11133.

The process may comprise the additional steps of deprotecting the N-terminal end and C-terminal end and/or cleaving the peptide in indistinct order from the polymer support using standard conditions and processes known in the art, after which the functional groups of said ends can be modified. Optional modification of the N-terminal end and C-terminal end can be performed with the peptide with formula (I) bound to the polymeric support or after the peptide has been cleaved from the polymer support.

Alternatively, $R_1$ may be introduced by the reaction of the N-terminal end of the peptide of the invention with a compound $R_1$—Z, wherein $R_1$ has the meaning described above and Z is a leaving group such as and not limited to, tosyl group, mesyl group and halogen groups among others; $R_1$ is introduced by nucleophilic substitution reaction in the presence of a base within a suitable solvent, wherein the fragments that have the functional groups not involved in the N—C bond formation are suitably protected with temporary or permanent protecting groups.

Optionally and/or additionally, $R_2$ radicals may be introduced by the reaction of a compound $HR_2$ wherein $R_2$ is —$OR_3$, —$NR_3R_4$ or —$SR_3$, with a complementary fragment corresponding to the peptide of formula (I) wherein $R_2$ is —OH in the presence of a suitable solvent and a base such as for example N,N-diisopropylethylamine (DIEA) or triethylamine or an additive such as 1-hydroxybenzotriazole (HOBt) or 1-hydroxyazabenzotriazole (HOAt) and a dehydrating agent, such as for example a carbodiimide, an uronium salt, a phosphonium salt or amidinium salt, among others, or by prior formation of an acyl halide with, for example, thionyl chloride, and thereby obtaining a peptide according to the invention with general formula (I), wherein the fragments that have the functional groups not involved in the N—C bond formation are suitably protected with temporary or permanent protecting groups, or alternatively other $R_2$ radicals can be introduced by means of the coupling simultaneous to the process for cleaving the peptide from the polymeric support.

The person skilled in the art will readily understand that the steps of deprotection/cleavage of the C-terminal end and N-terminal end and subsequent derivatization can be performed in indifferent order, according to procedures known in the art [Smith, M. B. and March, J. (1999) "*March's Advanced Organic Chemistry Reactions, Mechanisms and Structure*", 5th Edition, John Wiley & Sons, 2001].

The term "protecting group" refers to a group that blocks an organic functional group and which can be eliminated under controlled conditions. Protecting groups, their relative reactivities and the conditions under which they remain inert are known to the person skilled in the art.

Representative examples of protecting groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethoxycarbonyl (Troc), 2-(trimethylsilyl)ethyloxycarbonyl (Teoc), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Representative examples of protecting groups for carboxyl are esters such as tert-butyl ester (tBu), allyl ester (All), triphenylmethyl ester (trityl ester, Trt), cyclohexyl ester (cHex), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino)benzyl ester (Dmab), among others; preferred protecting groups of the invention are the esters of All, tBu, cHex, Bzl and Trt.

Trifunctional amino acids can be protected during the synthetic process with temporary or permanent protecting groups orthogonal to the protecting groups of the N-terminal end and C-terminal end.

The guanidine group of the arginine side chain can be protected with the allyloxycarbonyl (Alloc), para-toluenesulfonyl (Tosyl, Tos), 2,2,5,7,8-pentamethyl-croman-6-sulfonyl (Pmc), 2,2,4,6,7-pentamethyldihydrobenzofuran-5-sulfonyl (Pbf), nitro or 4-methoxy-2,3,6-trimethylbenzenesulfonyl (Mtr) groups, among others. The indole group of the tryptophan side chain can be protected with a formyl (For), tert-butyloxycarbonyl (Boc), mesitylen-2-sulphonyl (Mts) group or used unprotected. The hydroxyl group of the tyrosine side chain can be protected with 2-bromobenzyloxycarbonyl (2-BrZ), tert-butyl (tBu), allyl (All), benzyl (Bzl) or 2,6-dichlorobenzyl (2,6-diClZ) group among others.

In a preferred embodiment, the protecting group strategy used is the strategy wherein the amino groups are protected by Boc, the carboxyl groups are protected by Bzl, cHex or All, the arginine side chain is protected with Tos, the tryptophan side chain is protected with For or Mts and the tyrosine side chain is protected with 2-BrZ or Bzl.

In another preferred embodiment, the protecting group strategy used is the strategy wherein the amino groups are protected by Fmoc, the carboxyl groups are protected by tBu, All or Trt, the arginine side chain is protected with Pbf or Pmc, the tryptophan side chain is protected with Boc or is used unprotected, and the tyrosine side chain is protected with tBu.

Examples of these and other additional protecting groups, their introduction and their removal can be found in the literature [Greene T. W. and P. G. M. Wuts, (1999) "*Protective groups in Organic Synthesis*" John Wiley & Sons, New York, Atherton B. and Sheppard R. C. (1989) "*Solid Phase Peptide Synthesis: A practical approach*" IRL Oxford University Press]. The term "protecting groups" also includes polymeric supports used in solid phase synthesis.

When the synthesis takes place totally or partially on solid phase, the possible solid supports used in the method of the present invention involve polystyrene supports, polyethyleneglycol grafted on polystyrene and similar, such as for example and not limited to, p-methylbenzhydrylamine resins (MBHA) [Matsueda G. R. and Stewart J. M. (1981) "*A p-methylbenzhydrylamine resin for improved solid phase synthesis of peptide amides*" Peptides 2:45-50], 2-chlorotrityl resins [Barlos K., Gatos D., Kallitsis J., Papaphotiu G., Sotiriu P., Wenqing Y. and W. Schäfer (1989) "*Darstellung geschützter Peptid substituierter Fragmente unter Einsatz Triphenylmethyl Harze*" Tetrahedron Lett. 30:3943-3946; Barlos K., Gatos D., Kapolos S., Papaphotiu G., Schäfer W. and Wenqing Y. (1989) "*Veresterung von partiell geschützten Peptid fragment mit Harz. Einsatz von 2-Chlortritylchlorid zur Synthese von Leu1-Gastrin I*" Tetrahedron Lett. 30:3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxy-phenoxy)-valeric acid (PAL) [Albericio F., Kneib Cordonier N., Biancalana S., Gera L., Masada R. I., Hudson D. and Barany G. (1990) "*Preparation and application of the 5-(4-(9-fluorenylmethyloxycarbonyl)aminomethyl-3,5-dimethoxy-phenoxy)-valeric acid (PAL) handle for the solid phase synthesis of C-terminal peptide amides under mild conditions*" J. Org. Chem. 55.3730-3743], 2-[4-aminomethyl (2,4 dimethoxyphenyl)] phenoxy acetic acid (AM) [Rink H. (1987) "*Solid phase synthesis of protected peptide fragments using a diphenyl trialkoxy methylester resin*" Tetrahedron Lett. 28:3787-3790], Wang [Wang S. S. (1973) "*p-Alkoxybenzyl Alcohol Resin and p-Alkoxybenzyloxycarbonylhydrazide Resin for Solid Phase Synthesis of Protected Peptide Fragments*" J. Am. Chem. Soc. 95:1328-1333] and similar, allowing the simultaneous deprotection and cleavage of the peptide from the polymeric support.

Cosmetic or Pharmaceutical Compositions

The peptides of the invention can be administered to inibit the elastase activity and/or stimulate collagen synthesis in the skin, mucous membranes and/or scalp by any means that produce contact of the peptides with their site of action in the body of a mammal, preferably human, and in the form of composition that contains them.

In this regard, another aspect of the invention is a cosmetic or pharmaceutical composition comprising at least one peptide of general formula (I), its stereoisomers, mixtures thereof, and/or its cosmetically or pharmaceutically acceptable salts together with at least one cosmetically or pharmaceutically acceptable adjuvant. Such compositions can be prepared by conventional methods known to the person skilled in the art ["*Harry's Cosmeticology*", Eight Edition (2000) Rieger M. M., ed., New York Chemical Pub, NY, U.S.; "*Remington: The Science and Practice of Pharmacy, Twentieth Edition* (2003) Gennaro A. R., ed., Lippincott Williams & Wilkins, Philadelphia, U.S.].

The peptides of this invention have variable solubility in water, depending on the nature of their sequence or any possible modifications in the N-terminal end and/or C-terminal end. Therefore, the peptides of this invention can be incorporated into compositions by aqueous solution, and those that are not soluble in water can be solubilized in cosmetically or pharmaceutically acceptable conventional solvents such as for example and not limited to, ethanol, propanol, isopropanol, propylene glycol, glycerin, butylene glycol or polyethylene glycol or any combination thereof.

The cosmetically or pharmaceutically effective amount of the peptides of the invention to be administered, as well as their dosage, will depend on many factors, including the age, state of the patient, severity of the disorder or disease, the route and frequency of administration and the particular nature of the peptides to be used.

"Cosmetically or pharmaceutically effective amount" means a nontoxic but sufficient amount of peptide or peptides of the invention to provide the desired effect. The peptides of the invention are used in the cosmetic or pharmaceutical composition of this invention in cosmetically or pharmaceutically effective concentrations to achieve the desired effect; in a preferred form versus the total weight of the composition, between 0.00000001% (by weight) and 20% (by weight), preferably between 0.000001% (by weight) and 20% (by weight), more preferably between 0.0001% (by weight) and 10% (by weight) and even more preferably between 0.0001% (by weight) and 5% (by weight).

The peptides of the invention can also be incorporated in cosmetic or pharmaceutical delivery systems and/or sustained release systems.

The term "delivery systems" refers to a diluent, adjuvant, excipient or carrier with which the peptide of the invention is administered. These cosmetic or pharmaceutical carriers can be liquids such as water, oils or surfactants, including those of petroleum, animal, vegetable or synthetic origin, for example and not limited to, peanut oil, soybean oil, mineral oil, sesame oil, castor oils, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. "*Remington's Pharmaceutical Sciences*" by E. W. Martin describes diluents, adjuvants or excipients as appropriate vehicles.

The term "sustained release" is used in the conventional sense referring to a delivery system of a compound that provides the gradual release of the compound for a period of time and preferably, but not necessarily, with constant compound release levels throughout a period of time.

Examples of delivery systems or sustained release systems are liposomes, mixed liposomes, oleosomes, niosomes, miniparticles, milliparticles, microparticles, nanoparticles and solid lipid nanoparticles, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as microemulsions and nanoemulsions, for the purpose to achieve a greater penetration of the active principle and/or to improve its pharmacokinetic and pharmacodynamic properties. Preferred delivery systems or sustained release systems are liposomes, surfactant-phospholipid mixed micelles and microemulsions, more preferably water in oil microemulsions with internal structure of reverse micelle.

Sustained release systems can be prepared by methods known in the prior art, and compositions containing them can be administered, for example, by topical administration, including adhesive patches, non-adhesive patches and microelectric patches or by systemic administration, for example and not limited to, by via oral or parenteral, including nasal, rectal or subcutaneous implantation or injection, or direct implantation or injection into a specific body part, and preferably must release a relatively constant quantity of peptides of the invention. The amount of peptide contained in the sustained release system will depend, for example, on the site of administration, the kinetics and duration of the release of the peptide of the invention, as well as the nature of the condition, disorder and/or disease to be treated and/or prevented.

The peptides of this invention may also be adsorbed on solid organic polymers or solid mineral substrates such as for example and not limited to, talc, bentonite, silica, starch or maltodextrin among others.

The compositions containing the peptides of the invention can also be incorporated into fabrics, non-woven fabrics and medical devices that are in direct contact with skin, mucous membranes and/or scalp, so that they release the peptides of the present invention either by biodegradation of the anchoring system to the fabric or non-woven fabric or medical device or by friction with the body, by body moisture, by the pH of the skin or by body temperature. Furthermore, fabrics and non-woven fabrics can be used for making garments that are in direct contact with the body. Preferably, fabrics, non-woven fabrics and medical devices containing the peptides of the invention are used for the treatment and/or care of those conditions, disorders and/or diseases of the skin, mucous membranes and/or scalp that result from elastase activity and/or which benefit from stimulation of collagen synthesis.

Examples of fabrics, non-woven fabrics, garments, medical devices and means for immobilizing the peptides to them, including the delivery systems and/or sustained release systems described above can be found in the literature and are known in the state of the art [Schaab C. K. (1986) "*Impregnating Fabrics With Microcapsules*", HAPPI May 1986; Nelson G. (2002) "*Application of microencapsulation in textiles*" Int. J. Pharm. 242:55-62; "*Biofunctional Textiles and the Skin*" (2006) Curr. Probl. Dermatol. v. 33, Hipler U. C. and Elsner P., eds. S. Karger A. G., Basel, Switzerland; Malcom R. K.; McCullagh S. D., Woolfson A. D., Gorman S. P., Jones D. S. and Cuddy J. (2004) "*Controlled release of a model antibacterial drug from a novel self-lubricating silicone biomaterial*" J. Cont. Release 97:313-320]. Preferred fabrics, non-woven fabrics, garments and medical devices are bandages, gauzes, shirts, socks, stockings, underwear, girdles, gloves, diapers, sanitary towels, dressings, bedspreads, wipes, hydrogels, adhesive patches, non-adhesive patches, microelectric patches and/or facial masks.

The cosmetic or pharmaceutical compositions containing the peptides of this invention, their stereoisomers, mixtures thereof and/or their cosmetically or pharmaceutically acceptable salts, can be used in different types of compositions for topical or transdermal application optionally including cosmetically or pharmaceutically acceptable excipients necessary for formulating the desired administration form [Faulí i Trillo C. (1993) *Treatise of Galenic Pharmacy*, Luzán 5, S. A. Ediciones, Madrid].

The compositions for topical application or transdermal formulation may be presented in any solid, liquid or semi-solid formulation, such as for example, and not limited to, creams, multiple emulsions such as for example and not limited to, emulsions of oil and/or silicone in water, emulsions of water in oil and/or silicone, emulsions of water/oil/water type or water/silicone/water type and emulsions of oil/water/oil type or silicone/water/silica type, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencil, sprays or aerosols (sprays), including "leave on" formulations and "rinse off" formulations. These formulations for topical or transdermal application can be incorporated using techniques known by the person skilled in the art into different types of solid accessories, such as for example and not limited to, wipes, hydrogels, adhesive patches, non-adhesive patches, microelectric patches or facial masks, or can be incorporated into different makeup products such as makeup foundation, for example fluid foundation and compact foundation, makeup removal lotions, makeup removal milks, concealers, eye shadows; lipsticks, lip protectors, lip glosses and powders, among others.

The cosmetic or pharmaceutical compositions of the invention may include agents that increase the percutaneous absorption of the peptides of this invention, for example and not limited to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as for example injections by oxygen pressure, or any combination thereof, to achieve a greater penetration of the peptide of the invention. The area of application will be determined by the nature of the condition, disorder and/or disease to be prevented, cared and/or treated.

Furthermore, the cosmetic compositions containing the peptides of this invention, their stereoisomers and/or their cosmetically or pharmaceutically acceptable salts can be used in different types of formulations for oral administration, preferably in the form of oral cosmetics, for example and not limited to, capsules, including gelatin capsules, tablets, including sugar coated tablets, powders, granules, chewing gum, solutions, suspensions, emulsions, syrups, polysaccharide films, jellies or gelatins, and any other presentation known by the person skilled in the art. In particular, the peptides of the invention can be incorporated into any form of functional food or fortified food, such as and not limited to, in dietary bars or compact or noncompact powders. These powders can be solubilized in water, soda, dairy products, soy derivatives or be incorporated into dietary bars. The peptides of this invention may be formulated with common excipients and adjuvants for oral compositions or food supplements, such as and not limited to, fat components, aqueous components, humectants, preservatives, texturizing agents, flavors, aromas, antioxidants and common food dyes in the food industry.

The cosmetic or pharmaceutical compositions containing the peptides of the invention, their stereoisomers, mixtures thereof and/or their cosmetically or pharmaceutically acceptable salts can also be administered, by topical or transdermal route, by any other appropriate route, as for example oral or parenteral route, for which purpose they will include the pharmaceutically acceptable excipients necessary for the formulation of the desired administration form. In the context of this invention, the term "parenteral" includes the nasal, auricular, ophthalmic, rectal route, subcutaneous injections, intradermal, intravascular injections, such as intravenous, intramuscular, intravitreous, intraspinal, intracranial, intraarticular, intrathecal and intraperitoneal injections and any another similar injection or infusion technique. A review of the different pharmaceutical forms of administration of the active ingredients and excipients necessary for obtaining them can be found, for example, in the "*Tratado de Farmacia Galénica,*" *C. Fauli i Trillo,* 1993, Luzán 5, S. A. Ediciones, Madrid.

Among the cosmetically or pharmaceutically acceptable adjuvants contained in the cosmetic or pharmaceutical compositions described in this invention are included additional ingredients commonly used in compositions for the treatment and/or care of the skin, mucous membranes and/or scalp such as for example and not limited to, other elastase inhibiting agents, matrix metalloprotease inhibiting agents, melanin synthesis stimulating or inhibiting agents, whitening or depigmenting agents, propigmenting agents, self-tanning agents, antiaging agents, inhibiting agents of NO-synthase, inhibiting agents of 5α-reductase, inhibiting agents of lysyl- and/or prolyl-hydroxylase, antioxidants, free radical scavengers and/or agents against atmospheric pollution, reactive carbonyl species scavengers, anti-glycation agents, antihistamine agents, antiemetic agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, pigments or colorants, dyes, gelling polymers, thickeners, surfactants, softening agents, anti-wrinkle agents, agents able to reduce or treat the bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, such as for example agents stimulating collagen synthesis, agents stimulating the synthesis of elastin, agents stimulating the synthesis of decorin, agents stimulating the synthesis of laminin, agents stimulating the synthesis of defensins, agents stimulating the synthesis of chaperones, agents stimulating the synthesis of aquaporins, agents stimulating the synthesis of hyaluronic acid, agents stimulating the synthesis of fibronectin, agents stimulating the synthesis of sirtuins, agents stimulating the synthesis of lipids and components of the stratum corneum (ceramides, fatty acids, etc.), agents that inhibit collagen degradation, other agents that inhibit elastin degradation, agents that inhibit serine proteases such cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, agents stimulating the synthesis of glycosaminoglycans, antihyperkeratosis agents, comedolytic agents, antipsoriasis agents, DNA repairing agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, preservatives, perfumes, chelating agents, vegetable extracts, essential oils, marine extracts, agents obtained from a biofermentation process, mineral salts, cell extracts and sunscreens (organic or mineral photoprotective agents active against A and/or B ultraviolet rays) among others, provided they are physically and chemically compatible with the other components of the composition and especially with the peptides of general formula (I) contained in the composition of this invention. Furthermore, the nature of these additional ingredients should not unacceptably alter the benefits of the peptides of this invention. The nature of these additional ingredients can be synthetic or natural, such as vegetable extracts, or is obtained by a biofermentation process. Additional examples can be found described in the *CTFA International Cosmetic Ingredient Dictionary & Handbook*, 12th Edition (2008).

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one synthetic compound, natural extract or product obtained by a biofermentation process which is an elastase inhibiting agent, for example and not limited to, Elhibin® [INCI: Glycine Soja (Soybean) Protein], Preregen® [INCI: Glycine Soja (Soybean) Protein, Oxido Reductases] or Regu®-Age [INCI: Hydrolyzed Rice Bran Protein, Glycine Soja (Soybean) Protein, Oxido Reductases] marketed by Pentapharm/DSM, Juvenesce [INCI: Ethoxydiglycol and caprylic Triglycerid, Retinol, Ursolic Acid, Phytonadione, Ilomastat], Micromerol™ [INCI: Pyrus Malus Extract], Heather Extract [INCI: Calluna Vulgaris Extract], Extracellium® [INCI: Hydrolyzed Potato Protein] or Flavagrum™ PEG [INCI: PEG-6 Isostearate, Hesperetin Laurate] marketed by Coletica/Engelhard/BASF, Proteasyl® TP LS8657 [INCI: Pisum Sativum Extract] marketed by Laboratoires Sérobiologiques/Cognis, Sepilift DPHP [INCI: Dipalmitoyl hydroxyproline] marketed by SEPPIC, Vitaderm® [INCI: Alcohol, Water, Glycerin, Hydrolyzed Rice Protein, Ilex Aquifolium Extract, Sodium Ursolate, Sodium Oleanolate] marketed by Rahn, Gatuline® Age Defense 2 [INCI: Juglans Regia (Walnut) Seed Extract] marketed by Gattefosse, IP 2000 [INCI: Dextran, Trifluoroacetyl Tripeptide-2] marketed by IEB and Atrium, Radicaptol [INCI: Propylene Glycol, Water, Passiflora Incarnata Flower Extract, Ribes Nigrum (Blackcurrant) Leaf Extract, Vitis Vinifera (grape) Leaf Extract] marketed by Solabia or ViaPure™ Boswellia [INCI: Olivanum (Boswellia Serrata) Extract] marketed by Soliance, among others.

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one synthetic compound, natural extract or product obtained by a biofermentation process which is an agent stimulating collagen synthesis agent, for example and not limited to, ascorbic acid and the derivatives thereof such as ascorbyl palmitate, magnesium ascorbyl phosphate, sodium ascorbyl phosphate and ascorbyl alpha- and beta-glucoside, retinol and derivatives of retinol such as retinoic acid, retinal, retinyl acetate or retinyl palmitate, vegetable extracts such as for example extracts of *Aloe* and *Centella* species, carnitine, carnosine, creatine, asiatic acid, madecassic acid, madecassoside, asiaticoside, extracts of *Centella asiatica*, niacinamide, astaxanthine, glucans, soy extract and soy isoflavones, such as genistein and daidzein, rutin, chrysin, morin, betel nut alkaloids, forskolin, betulinic acid, extracts of *Plantago* species, TGF-beta, extracts of *Ginkgo biloba*, glutamine, glycolic acid, Matrixyl® [INCI: Palmitoyl Pentapeptide-4]; Matrixyl 3000® [INCI: Palmitoyl Tetrapeptide-7, Palmitoyl oligopeptide] or Dermaxyl® [INCI: C12-15 Alkyl Benzoate, Tribehenin, Ceramide 2, PEG 10 Rapeseed Sterol, Palmitoyl Oligopeptide] marketed by Sederma/Croda, Syn®-Coll [INCI: Palmitoyl Tripeptide-5], Phytaluronate® [INCI: Locust Bean (Ceratonia Siliqua) Gum] or BeauActive™ MTP [INCI: Hydrolyzed milk protein] marketed by Pentapharm/DSM, Thalassine™ [INCI: Algae Extract] marketed by Biotechmarine, EquiStat™ [INCI: Pyrus Malus Fruit Extract, Glycine Soja Seed Extract] or Juvenesce [INCI: Ethoxydiglicol and caprylic Triglycerid, Retinol, Ursolic Acid, Phytonadione, Ilomastat] marketed by Coletica/Engelhard/BASF, SMS Anti-wrinkle® [INCI: Oligopeptides purified from Annona Squamosa] or Papilactyl D® [INCI: Water, Cyperus Esculentus Tuber Extract] marketed by Silab, ChroNOline™ [INCI: Glycerin, Water (Aqua), Dextran, Caprooyl Tetrapeptide-3], Kollaren® [INCI: Tripeptide-1] or Thymulen®4 [INCI: Water, Dextran, Acetyl Tetrapeptide-2] marketed by Atrium Innovations/Unipex Group, BioLyse T.A. [INCI: Original Oligopeptide, composed by L-lisine and L-arginine] or Peptiskin® [INCI: Arginine/Lysine polypeptide] marketed by Solabia, Gatuline® In-Tense [INCI: Caprylic/Capric Triglyceride, Spilanthes Acmella Flower Extract] marketed by Gattefossé, PhytoCellTec™ Malus Domestica [INCI: Malus Domestica Fruit Cell Culture, Xanthan Gum, Glycerin, Lecithin, Phenoxyethanol, Aqua] marketed by Mibelle Biochemistry, Phytosphingosine SLC [INCI: Salicyloyl Phytosphingosine] marketed by Evonik Goldschmidt, Dakaline [INCI: Prunus Amygdalus Dulcis, Anogeissus Leiocarpus Bark Extract] marketed by Soliance, Collaxyl® [INCI: Hexapeptide-9], GP4G [INCI: Artemia Extract], D'Orientine™ [INCI: Phoenix Dactylifera (Date) Seed Extract] or Ederline™ [INCI: Pyrus Malus Apple Fruit Extract] marketed by Vincience, or Homeostatine [INCI: Enteromorpha Compressa, Caesalpinia Spinosa] marketed by Provital.

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one synthetic compound, natural extract or product obtained by a biofermentation process which is a reactive carbonyl species scavenger, free radical scavenger and/or anti-glycation agent, such as for example and not limited to, carnosine and its derivatives, GHK [INCI: Tripeptide-1] and its salts and/or derivatives, or Aldenine® [INCI: Hydrolized Wheat Protein, Hydrolized Soy Protein, Tripeptide-1] or Preventhelia™[INCI: Diaminopropionyl Tripeptide-33] marketed by Lipotec, among others.

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one extract which is an anti-wrinkle agent and/or anti-aging agent, for example and not limited to, extracts of *Vitis vinifera, Rosa canina, Curcuma longa, Iris pellicle, Theobroma cacao, Ginkgo biloba, Leontopodium Alpinum* or *Dunaliella salina* among others, or at least one synthetic compound or product that is an anti-wrinkle or anti-aging agent, for example and not limited to, Matrixyl® [INCI: Palmitoyl Pentapeptide-3], Matrixyl 3000® [INCI: Palmitoyl Tetrapeptide-7, Palmitoyl Oligopeptide], Essenskin™ [INCI: Calcium Hydroxymethionine], Renovage [INCI: Teprenone] or Dermaxyl® [INCI: Palmitoyl Oligopeptide] marketed by Sederma/Croda, Vialox® [INCI: Pentapeptide-3], Syn Ake® [INCI: Dipeptide Diaminobutyroyl Benzylamide Diacetate], Syn®-Coll [INCI: Palmitoyl Tripeptide-5], Phytaluronate [INCI: Locust Bean (Ceratonia Siliqua) Gum] or Preregen®

[INCI: Glycine Soja (Soybean) Protein, Oxido Reductase] marketed by Pentapharm/DSM, Myoxinol™[INCI: Hydrolyzed Hibiscus Esculentus Extract], Syniorage™ [INCI: Acetyl Tetrapeptide-11], Dermican™ [INCI: Acetyl Tetrapeptide-9] or DN-AGE™ LS [INCI: Cassia Alata Leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide 18], Inyline™ [INCI: (proposed) Acetyl Hexapeptide-30], Aldenine® [INCI: Hydrolized Wheat Protein, Hydrolized Soy Protein, Tripeptide-1], Preventhelia™ [INCI: Diaminopropionoyl Tripeptide-33], Decorinyl™ [INCI: Tripeptide-10 Citrulline], Trylagen™ [INCI: Pseudoalteromonas Ferment Extract, Hydrolyzed Wheat Protein, Hydrolyzed Soy Protein, Tripeptide-10 Citrulline, Tripeptide-1]; Eyeseryl® [INCI: Acetyl Tetrapeptide-5], Peptide AC29 [INCI: Acetyl Tripeptide-30 Citrulline], Lipochroman-6 [INCI: Dimethylmethoxy Chromanol], Chromabright™ [INCI: Dimethylmethoxy Chromanyl Palmitate], Vilastene™ [INCI: Lysine HCl, Lecithin, Tripeptide-10 Citrulline], dGlyAGE™ [INCI: Lysine HCl, Lecithin, Tripeptide-9 Citrulline] or Antarcticine® [INCI: Pseudoalteromonas Ferment Extract] marketed by Lipotec, Kollaren® [INCI: Tripeptide-1, Dextran] marketed by Institut Europeen de Biologie Cellulaire, Collaxyl® IS [INCI: Hexapeptide-9], Orsirtine™ GL [INCI: Oryza Sativa (Rice) Extract], D'Orientine™ IS [INCI: Phoenix Dactylifera (Date) Seed Extract], Phytoquintescine™ [INCI: Einkorn (Triticum monococcum) Extract] or Quintescine™ IS [INCI: Dipeptide-4] marketed by Vincience, BONT-L Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: Acmella oleracea Extract], Gatuline® In-Tense [INCI: Spilanthes Acmella Flower Extract] or Gatuline® Age Defense 2 [INCI: Juglans Regia (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: Pyrus Malus Fruit Extract, Glycine Soja Seed Extract] or Juvenesce [INCI: Ethoxydiglycol and Caprylic Triglycerid, Retinol, Ursolic Acid, Phytonadione, Ilomastat] marketed by Coletica/Engelhard/BASF, Ameliox [INCI: Carnosine, Tocopherol, Silybum Marianum Fruit Extract] or PhytoCellTec Malus Domestica INCI: Malus Domestica Fruit Cell Culture] marketed by Mibelle Biochemistry, Bioxilift [INCI: Pimpinella Anisum Extract] or SMS Anti-Wrinkle® [INCI: Annona Squamosa Seed Extract marketed by Silab, $Ca^{2+}$ channel antagonists such as, for example and not limited to, alverine, manganese or magnesium salts, certain secondary or tertiary amines, retinol and its derivatives, and idebenone and its derivatives, coenzyme Q10 and its derivatives, boswellic acid and its derivatives, GHK and its derivatives and/or salts, carnosine and its derivatives, DNA repair enzymes such as, for example and not limited to, photolyase or T4 endonuclease V, or chloride channel agonists among others.

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one synthetic or natural extract which is an anti-cellulite agent, lipolytic agent and/or venotonic agent such as for example, and not limited to, extracts or hydrolysates of extracts of *Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix* (ivy extract), *Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus* (butcher's broom extract), *Sambucus Nigra, Spirulina Platensis* Algae, *Uncaria Tomentosa* or *Verbena Officinalis* among others, or, in addition, at least a synthetic compound, extract or product obtained by a biofermentation process that is an anti-cellulite agent, lipolytic agent and/or venotonic agent, for example and not limited to, dihydromyricetin, coenzyme A, lipase, glaucin, esculin, visnadine, Regu®-Shape [INCI: Isomerized Linoleic Acid, Lecithin, Glycerin, Polysorbate 80] marketed by Pentapharm/DSM, UCPeptide™ V [INCI: Pentapeptide] or AT Peptide™ IS [INCI: Tripeptide-3] marketed by Vincience/ISP, Adiposlim [INCI: Sorbitan Laurate, Lauroyl Proline] marketed by SEPPIC, Liporeductyl® [INCI: Lecithin, Caffeine, Butcherbroom (Ruscus Aculeatus) Root Extract, Tea-Hydroiodide, Ivy (Hedera Helix) Extract, Carnitine, Escin, Tripeptide-1] marketed by Lipotec, caffeine, carnitine, escin and/or iodide triethanolamine, among others.

Applications

Another aspect of this invention relates to the use of at least one of the peptides of general formula (I), their stereoisomers, mixtures thereof and/or their cosmetically or pharmaceutically acceptable salts in the preparation of a cosmetic or pharmaceutical composition for the treatment and/or care of skin, mucous membranes and/or scalp.

Additionally, this invention relates to the use of at least one of the peptides of general formula (I), their stereoisomers, mixtures thereof and/or their cosmetically or pharmaceutically acceptable salts in the preparation of a cosmetic or pharmaceutical composition for the inhibition of elastase and/or stimulation of collagen synthesis, preferably in the skin, mucous membranes and/or scalp.

Furthermore, another aspect of this invention relates to the use of at least one of the peptides of general formula (I), their stereoisomers, mixtures thereof and/or their cosmetically or pharmaceutically acceptable salts in the preparation of a cosmetic or pharmaceutical composition for the treatment, prevention and/or care of conditions, disorders and/or diseases of the skin, mucous membranes and/or scalp that result from elastase activity and/or which benefit from stimulation of collagen synthesis, preferably in the skin, mucous membranes and/or scalp.

Preferably, among the conditions, disorders and/or diseases of the skin, mucous membranes and/or scalp to treat, prevent and/or care due to elastase activity and/or which benefit from stimulation of collagen synthesis are wrinkles, expression wrinkles, stretch marks, skin aging, skin photoaging, wound healing disorders, ulcers, diabetic ulcers, keloids, hypertrophic scars, acne, cellulite, orange peel skin, elastosis, actinic elastosis, keratosis, inflammation, dermatitis, atopic dermatitis, allergic contact dermatitis, sensitive skin, eczema, bullous pemphigoid, gingivitis, periodontitis, skin cancer, tumor invasions, tumour metastasis, telangiectasia, couperosis, varicose veins, eye dark circles, bags under the eye, alopecia and hair loss, rosacea and/or psoriasis.

According to a preferred embodiment, this invention relates to the use of a peptide of formula (I) in the preparation of a cosmetic or pharmaceutical composition for the treatment of skin, mucous membranes and/or scalp to reduce, delay and/or prevent the signs of aging and/or of photoaging.

According to another preferred embodiment, this invention relates to the use of at least one of the peptides of general formula (I), their stereoisomers, mixtures thereof, and/or their cosmetically or pharmaceutically acceptable salts in the preparation of a cosmetic or pharmaceutical composition that increases the elasticity of the skin, mucous membranes and/or scalp.

In another particular aspect, this invention relates to the use of at least one of the peptides of general formula (I), their stereoisomers, mixtures thereof, and/or their cosmetically or pharmaceutically acceptable salts in the preparation of a cosmetic or pharmaceutical composition that reduces or eliminates facial wrinkles.

According to another preferred embodiment, this invention relates to the use of at least one of the peptides of general formula (I), their stereoisomers, mixtures thereof and/or their cosmetically or pharmaceutically acceptable salts in the preparation of a cosmetic or pharmaceutical composition for hair treatment or hair hygiene. Examples of cosmetic or pharmaceutical composition for hair treatment or hair hygiene include shampoos, conditioners, hair lotions, hair tonics or masks for the scalp, among others.

According to another preferred embodiment, this invention relates to the use of at least one of the peptides of general formula (I), their stereoisomers, mixtures thereof, and/or their cosmetically or pharmaceutically acceptable salts in the preparation of a cosmetic or pharmaceutical composition for the body hygiene or treatment and/or care of the skin of the face and/or the body. Examples of cosmetic or pharmaceutical composition for the body hygiene or the treatment and/or care of the skin of the face and/or the body include creams, multiple emulsions such as, for example and not limited to, emulsions of oil and/or silicone in water, emulsions of water in oil and/or silicone, emulsions of water/oil/water type or water/silicone/water type and emulsions of oil/water/oil type or silicone/water/silica type, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays or aerosols (sprays), including "leave on" formulations and "rinse off" formulations, wipes, hydrogels, adhesive patches, non-adhesive patches, microelectric patches or facial masks, makeup products such as makeup foundation, for example fluid foundation and compact foundation, makeup removal lotions, makeup removal milks, concealers, eye shadows, lipsticks, lip protectors, lip glosses and powders, among others.

The compositions containing the peptides of this invention, their stereoisomers, mixtures thereof and/or their cosmetically or pharmaceutically acceptable salts can be applied to the skin, mucous membranes and/or scalp or administered orally or parenterally as necessary to treat, prevent and/or care for a condition, disorder and/or disease.

The cosmetic or pharmaceutical compositions concerned by this invention can be applied to the skin and/or scalp by iontophoresis, sonophoresis, electroporation, microelectric patches, mechanical pressure, osmotic pressure gradient, occlusive cure, microinjections or needle-free injections by means of pressure, such as for example injections by oxygen pressure, or any combination thereof, to achieve a greater penetration of the peptide of the invention.

An additional aspect of this invention relates to a cosmetic or pharmaceutical method for the treatment, prevention and/or care of conditions, disorders and/or diseases of mammals, preferably humans, which benefit from the inhibition of elastase and/or stimulation of collagen synthesis, which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing it. This invention also provides a cosmetic or pharmaceutical method for inhibiting elastase and/or stimulating collagen synthesis, preferably in the skin, mucous membranes and/or scalp. Furthermore, this invention provides a cosmetic or pharmaceutical method for increasing the elasticity of the skin, mucous membranes and/or scalp. An additional aspect of this invention relates to a cosmetic or pharmaceutical method for reducing or eliminating facial wrinkles.

Moreover, this invention provides a method for the cosmetic or pharmaceutical treatment, prevention and/or care for conditions, disorders and/or diseases of skin, mucous membranes and/or scalp which are the result of elastase activity and/or which benefit from stimulation of collagen synthesis, including the topical or transdermic application on the skin, mucous membranes and/or scalp or oral or parenteral administration of a cosmetic or pharmaceutical composition containing at least one peptide of the invention, its stereoisomers, mixtures thereof and/or its cosmetically or pharmaceutically acceptable salts.

The frequency of the application or administration can vary widely, depending on the needs of each subject, with recommendation for a range of application or administration from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

ABBREVIATIONS

The abbreviations used for amino acids follow the rules of the Commission on Biochemical Nomenclature of the IUPAC-IUB specified in *Eur. J. Biochem.* (1984) 138:9 37 and *J. Biol. Chem.* (1989) 264:633-673.

®, resin; Ac, acetyl; Adpoc, 1-(1-adamantyl)-1-methylethoxy-carbonyl; Ala, alanine; All, allyl; Alloc, allyloxycarbonyl; AM, 2-[4-aminomethyl-(2,4-dimethoxyphenyl)] phenoxyacetic acid; Arg, arginine; Boc, tert-butyloxycarbonyl; 2-BrZ, 2-bromobenzyloxycarbonyl; BSA, bovine seroalbumine; Bzl, benzyl; Cbz, benzyloxycarbonyl; cHx, cyclohexyl; Cit, citrulline; ClTrt-®, 2-chlorotrityl resin; ClZ, 2-chlorobenzyl; cps, centipoise; C-terminal, carboxy-terminal; DCM, dichloromethane; Dde, N'-[1-(4,4-dimethyl-2,6-dioxocyclohex-1-ylidene)ethyl; 2,6-diClZ, 2,6-dichlorobenzyloxycarbonyl; DIEA, N,N-diisopropylethyl amine; DIPCDI, N,N'-diisopropylcarbodiimide; Dmab, 4-(N-[1-(4,4-dimethyl-2,6-dioxocyclohexylidene)-3-methylbutyl] amino)benzyl; DMF, N,N-dimethylformamide; DMSO, dimethylsulfoxide; DNP, 2,4-dinitrophenyl; DPPC, dipalmitoylphosphatidylcholine; ECM, extracellular matrix; EDTA, ethylenediaminetetraacetic acid; ELISA, Enzyme-Linked Immunosorbent Assay; equiv, equivalent; ES-MS, electrospray ionization mass spectrometry; Fm, fluorenylmethyl; Fmoc, 9-fluorenylmethyloxycarbonyl; GAG, glycosaminoglycan; Gly, glycine; HLE, human leukocyte elastase; HOBt, 1-hydroxybenzotriazole; HPLC, high-performance liquid chromatography; INCI: International Nomenclature of Cosmetic Ingredients; ivDde, 1-(4,4-dimethyl-2,6-dioxo-cyclohexyliden)-3-methyl-butyl; MAGP, microfibril-associated glycoprotein; MBHA, p-methylbenzhydrylamine; MeCN, acetonitrile; MeOH, methanol; MLV, multilayered vesicles; MMP, matrix metalloprotease, Mtr, 4-methoxy-2,3,6-trimethylbenzenesulfonyl; Mtt, methyltritile or methoxytritile; Nle, norleucine; N-terminal, amino terminal; PAL, 5-(4-(aminomethyl)-3,5-bis(methoxy)phenoxy)valeric acid; Palm, palmitoyl; Pbf, 2,2,4,6,7-pentamethyl-dihydrobenzofuran-5-sulfonyl; PBS, phosphate buffered saline; Phg, phenylglycine; Pmc, 2,2,5,7,8-pentamethylchroman-6-sulfonyl; pNZ, para-nitrobenzyloxycarbonyl; q.s., sufficient quantity; q.s.p., sufficient quantity for, tBu, tert-butyl; Teoc, 2-(trimethylsilyl)ethyloxycarbonyl; TFA, trifluoroacetic acid; THF, tetrahydrofuran; TIS, triisopropylsilane; Tos, para-toluenesulfonyl or tosyl; Troc, 2,2,2-trichloroethoxycarbonyl; Trp, tryptophan; Trt, triphenylmethyl or Trityl; Tyr, tyrosine; ULV, unilamellar vesicles; UV, ultraviolet; Val, valine; Z, benzyloxycarbonyl.

Chemical Synthesis

All synthetic processes are carried out in polypropylene syringes fitted with discs of porous polyethylene or Pyrex® reactors fitted with porous plates. Solvents and soluble reagents are removed by suction. The Fmoc group is removed with piperidine-DMF (2:8, v/v) (1×1 min, 1×5 min, 5 mL/g resin) [Lloyd Williams P., Albericio F. and Giralt E. (1997) "Chemical Approaches to the Synthesis of Peptides and Proteins" CRC, Boca Raton, Fla., USA]. Washes between steps of deprotection, coupling, and, again, deprotection, were carried out with DMF (3×1 min) each time using 10 mL solvent/g resin. Coupling reactions were performed with 3 mL solvent/g resin. The control of the couplings is done by the ninhydrin test [Kaiser E., Colescott R. L., Bossing C. D. and Cook P. I. (1970) Color test for detection of free terminal amino groups in the solid phase synthesis of peptides, "Anal. Biochem. 34:595 598]. All synthetic reactions and washes were carried out at room temperature.

HPLC chromatographic analysis was carried out on Shimadzu equipment (Kyoto, Japan) using a reversed-phase column thermostatized at 30° C. (250×4.0 mm, Kromasil $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm.

Example 1

Obtaining Fmoc-$X_n$-$AA_1$-$AA_2$-$AA_3$-$AA_4$-$Y_m$-O-2-ClTrt-®, Wherein $AA_4$ is -L-Phg-, -D-Phg- or -Gly-, $AA_3$ is -L-Trp-, -L-Tyr- or -L-Val-; $AA_2$ is -L-Ala-, -L-Cit-, -L-Nle-, -L-Phg- or -D-Phg-; $AA_1$ is -L-Arg-, -L-Phg-, -D-Phg- or -L-Nle-; and n and m are 0.

3.29 g of Fmoc-L-Phg-OH, 3.29 g of Fmoc-D-Phg-OH or 2.61 g of Fmoc-Gly-OH (8.8 mmol; 1 equiv), dissolved in 55 ml of DCM to which was added 1.3 ml of DIEA (7.6 mmol; 0.86 equiv), were coupled onto dry 2-chlorotrityl resin (5.5 g; 8.8 mmol). The suspension was stirred for 5 min, after which 2.5 mL of DIEA were added (14.6 mmol; 1.66 equiv). The mixture was allowed to react for 40 min. Remaining chloride groups were blocked by treatment with 4.4 mL of MeOH.

The Fmoc N-terminal end group was deprotected as described in general methods and 9.38 g of Fmoc-L-Trp-OH, 10.11 g of Fmoc-L-Tyr(tBu)-OH or 7.47 g of Fmoc-L-Val-OH (22 mmol, 2.5 equiv) were coupled onto the peptidyl resin in the presence of DIPCDI (3.39 mL, 22 mmol, 2.5 equiv) and HOBt (3.37 g, 22 mmol, 2.5 equiv) using DMF as solvent for 1 hour. The resin was then washed as described in general methods and the deprotection treatment of the Fmoc group was repeated to couple the next amino acid. According to the protocols described, we coupled sequentially 6.85 g of Fmoc-L-Ala-OH, 8.74 g of Fmoc-L-Cit-OH, 7.77 g of Fmoc-L-Nle-OH, 8.21 g of Fmoc-L-Phg-OH or 8.21 g of Fmoc-D-Phg-OH (22 mmol, 2.5 equiv) and then 14.27 g of Fmoc-L-Arg-(Pbf)-OH, 8.21 g of Fmoc-L-Phg-OH, 8.21 g of Fmoc-D-Phg-OH or 7.77 g of Fmoc-L-Nle-OH (22 mmol, 2.5 equiv) in the presence, in each coupling, of 3.37 g of HOBt (22 mmol, 2.5 equiv) and 3.39 mL of DIPCDI (22 mmol, 2.5 equiv).

After the synthesis, the peptidyl resins were washed with DCM (5×3 min) and dried by nitrogen stream.

Example 2

Prophetic

Obtaining Fmoc-$X_n$-$AA_1$-$AA_2$-$AA_3$-$AA_4$-$Y_m$-AM-MBHA-®, Wherein $AA_4$ is -L-Phg-, -D-Phg- or -Gly-; $AA_3$ is -L-Trp-, -L-Tyr- or -L-Val-; $AA_2$ is -L Ala-, -L-Cit-, -L-Nle-, -L-Phg- or -D-Phg-; $AA_1$ is -L-Arg-, -L-Phg-, -D-Phg- or -L-Nle-; and n and m are 0.

6.85 g of Fmoc-AM-MBHA resin with a loading of 0.73 mmol/g (5 mmol) are treated with piperidine-DMF according to the general protocol described in order to remove the Fmoc group. Onto the deprotected resin are incorporated 9.33 g of Fmoc-L-Phg-OH, 9.33 g of Fmoc-D-Phg-OH or 7.43 g of Fmoc-Gly-OH (25 mmol; 5 equiv) using DIPCDI (3.85 mL, 25 mmol; 5 equiv) and HOBt (3.85 g, 25 mmol; 5 equiv) and DMF as solvent for 1 hour.

The resin is then washed as described in general methods and the deprotection treatment of the Fmoc group is repeated to couple the next amino acid. Following the previously described protocols 10.67 g of Fmoc-L-Trp-OH, 11.49 g of Fmoc-L-Tyr-(tBu)-OH or 8.49 g of Fmoc-L-Val-OH (25 mmol; 5 equiv); 9.33 g Fmoc-L-Phg-OH, 9.33 g of Fmoc-D-Phg-OH, 7.78 g of Fmoc-L-Ala-OH, 9.94 g of Fmoc-L-Cit-OH or 8.84 g of Fmoc-L-Nle-OH (25 mmol; 5 equiv) and subsequently 16.22 g of Fmoc-L-Arg-(Pbf)-OH, 9.33 g of Fmoc-L-Phg-OH, 9.33 g of Fmoc-D-Phg-OH or 8.84 g of Fmoc-L-Nle-OH (25 mmol; 5 equiv) are coupled sequentially in the presence in each coupling of 3.85 g of HOBt (25 mmol; 5 equiv) and 3.85 mL of DIPCDI (25 mmol; 5 equiv).

After the synthesis, the peptidyl resins are washed with DCM (5×3 min) and dried by nitrogen stream.

Example 3

General Procedure for Fmoc N-Terminal Protecting Group Removal.

The Fmoc N-terminal end group of the peptidyl resins obtained in Example 1 was deprotected as described in general methods (20% piperidine in 1×5 min+1×20 min). The peptidyl resins were washed with DMF (5×1 min), DCM (4×1 min), diethyl ether (4×1 min) and dried under vacuum.

The same process could have been applied to the N-terminal Fmoc group of the peptidyl resins obtained in prophetic Example 2.

Example 4

Prophetic

Procedure for Introducing the $R_1$ Palmitoyl Group on the Peptidyl Resin Obtained in Example 3.

2.56 g of palmitic acid (10 mmol; 10 equiv) predissolved in DMF (1 mL) are added onto 1 mmol of peptidyl resins obtained in Example 3 in the presence of 1.53 g of HOBt (10 mmol; 10 equiv) and 1.54 mL DIPCDI (10 mmol; 10 equiv). They are allowed to react for 15 hours, after which the resin is washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and dried under vacuum.

Example 5

Procedure for Introducing the Acetyl Group $R_1$ on the Peptidyl Resin Obtained in Example 3.

1 mmol of peptidyl resin obtained in Example 3 was treated with 25 equiv of acetic anhydride in the presence of 25 equiv of DIEA using 5 mL of DMF as solvent. It was allowed to react for 30 min, after which the peptidyl resins were washed with DMF (5×1 min), DCM (4×1 min), diethyl ether (4×1 min) and dried under vacuum.

Example 6

Cleavage Procedure of Peptidyl Resins Obtained in Examples 3, 4 and 5.

200 mg of the dried peptidyl resin obtained in example 5 were treated with 5 mL of TFA-TIS-$H_2O$ (90:5:5) for 2 h at room temperature with stirring. Filtrates were collected onto 50 mL cold diethyl ether, filtered through polypropylene syringes fitted with porous polyethylene discs and washed 5 times with 50 mL diethyl ether. The final precipitates were dried under vacuum.

HPLC analysis of peptides obtained in gradients of MeCN (+0.07% TFA) in $H_2O$ (+0.1% TFA) showed a purity exceeding 80% in all cases. The identity of the peptides obtained was confirmed by ES-MS. The same process could have been applied to the peptidyl resins obtained in Examples 3 and 4.

Example 7

Prophetic

Cleavage Procedure of the Polymer Support and Derivatization with $R_2$ Substituted amine: Obtaining Ac-$X_n$-$AA_1$-$AA_2$-$AA_3$-$AA_4$-$Y_m$—NH—$(CH_2)_{15}$—$CH_3$, wherein $AA_4$ is -L-Phg-, -D-Phg- or -Gly-; $AA_3$ is -L-Trp-, -L-Tyr- or -L-Val-; $AA_2$ is -L-Ala-, -L-Cit-, -L-Nle-, -L-Phg- or -D-Phg-; $AA_1$ is -L-Arg-, -L-Phg-, -D-Phg- or -L-Nle-; and n and m are 0.

The peptides Ac-$X_n$-$AA_1$-$AA_2$-$AA_3$-$AA_4$-$Y_m$-OH with fully protected side chains are obtained by treating 150 mg of peptidyl resin Ac-$X_n$-$AA_1$-$AA_2$-$AA_3$-$AA_4$-$Y_m$-O-2-ClTrt-® of Example 5, previously dried under vacuum in the presence of KOH, with 3 mL of a 3% solution of TFA in DCM for 5 min. The filtrates are collected onto 50 mL of cold diethyl ether and the treatment is repeated three times. Ethereal solutions are evaporated under vacuum to dryness at room temperature, the precipitates are dissolved in 50% MeCN in $H_2O$ and lyophilized. 10 mg of the crude products obtained are weighed in a flask and 3 equiv of hexadecylamine and 25 mL of anhydrous DMF are added. 2 equiv of DIPCDI are added, and allowed to react with magnetic stirring at 47° C. Reactions are monitored by HPLC for disappearance of the initial product, which is complete after 24-48 h. Solvents wore are evaporated to dryness and coevaporated twice with DCM. The residues obtained [Ac-$X_n$-$AA_1$-$AA_2$-$AA_3$-$AA_4$-$Y_m$—NH—$(CH_2)_{15}$—$CH_3$ with side chains fully protected] are resuspended in 25 mL of a mixture of DCM-TFA-anisole (49:49:2) and allowed to react for 30 min at room temperature. They are added onto 250 mL of cold diethyl ether, the solvents are evaporated at reduced pressure and two additional coevaporations with ether are made. The residues are dissolved in a mixture of 50% MeCN in $H_2O$ and lyophilized.

HPLC analysis of peptides obtained in gradients of MeCN (+0.07% TFA) in $H_2O$ (+0.1% TFA) showed a purity exceeding 70% in all cases.

Example 8

Elastase Inhibition Assay.

The peptides were resuspended in water in the presence of 0.5% DMSO. The assay was conducted on black microplates with 96 wells using the EnzChek® Elastase Assay Kit (Molecular Probes). For this purpose, the peptides were pre-incubated at 0.1 mM for 1 hour with 0.4 unit/mL of elastase at room temperature with moderate stirring, after which the conjugated substrate was added to fluorescein (DQ™ Elastin) at a final concentration of 25 μg/mL and reactions were incubated for 2 h at room temperature with stirring and protected from light. The substrate, whose fluorescence is inhibited, is digested by elastase to release fluorescent fragments which are monitored by fluorescence with a FLUOstar galaxy reader (BMG LabTechnologies) using 485 nm filters for excitation and 530 nm filters for emission.

Table 2 lists the peptides that showed inhibition values above 45%. Inhibition values were normalized with respect to baseline values of average inhibition.

TABLE 2

| Elastase inhibition percentage | |
|---|---|
| Peptide | % inhibition |
| Ac-Phg-Phg-L-Val-Phg-OH | 76.1 |
| Ac-Phg-Phg-L-Val-Gly-OH | 64.2 |
| Ac-Phg-Phg-L-Trp-Phg-OH | 84.2 |
| Ac-Phg-Phg-L-Trp-Gly-OH | 65.0 |
| Ac-L-Nle-Phg-L-Val-Phg-OH | 73.8 |
| Ac-L-Nle-Phg-L-Val-Gly-OH | 62.7 |
| Ac-L-Nle-Phg-L-Trp-Phg-OH | 90.0 |
| Ac-L-Nle-Phg-L-Trp-Gly-OH | 69.6 |
| Ac-L-Arg-Phg-L-Val-Phg-OH | 82.3 |
| Ac-L-Arg-Phg-L-Val-Gly-OH | 81.4 |
| Ac-L-Arg-Phg-L-Trp-Phg-OH | 90.3 |
| Ac-L-Arg-Phg-L-Trp-Gly-OH | 66.9 |
| Ac-Phg-L-Trp-Phg-OH | 45.1 |

Example 9

Human Elastase Inhibition Assay.

Human neutrophil elastase was reconstituted at 5 /vg/mL in 50 mM sodium acetate, 200 mm NaCl, pH 5.5 buffer. 0.2 µg/ml of protease were preincubated with the peptides at a final concentration of 0.05-2 mM in a black microplate with 96 wells for 1 hour at room temperature. After preincubation, 25 µg/mL of substrate (MeOSuc-Ala-Ala-Pro-Val aminomethyl coumarin) were added to the wells and the samples were incubated for 2 h at room temperature and protected from light. The fluorescence released by digestion of the substrate was measured with an automated multiplate fluorescence reader, exciting at 370 nm and reading at 460 nm.

The results were corrected from the baseline fluorescence value in the absence of elastase and product, and were normalized with respect to the fluorescence of the control, and the minimum inhibitory concentration for each of the peptides was determined. Table 3 lists the best inhibition values of obtained for the peptides.

TABLE 3

Minimum inhibitory concentration of peptides against human elastase

| Peptide | IC50 (mM) |
|---|---|
| H-L-Arg-Phg-L-Val-Phg-OH | 0.094 |
| H-L-Arg-Phg-L-Val-Gly-OH | 0.407 |
| H-L-Arg-Phg-L-Trp-Phg-OH | 0.103 |

Example 10

Prophetic

Preparation of a Cosmetic Composition Containing Palm-L-Nle-Phg-L-Tyr-Phg-$NH_2$.

| | INGREDIENT (INCI Nomenclature) | % IN WEIGHT |
|---|---|---|
| A | MINERAL OIL | 8.0 |
| A | STEARIC ACID | 2.4 |
| A | CETEARYL ALCOHOL | 1.6 |
| A | BEESWAX | 0.8 |
| B | GLYCERINE | 2.4 |
| B | AQUA (WATER) | 63.4 |
| C | CARBOMER | 0.3 |
| C | TRIETHANOLAMINE | 0.9 |
| D | AQUA (WATER) | 15.0 |
| D | Palm-L-Nle-Phg-L-Tyr-Phg-$NH_2$ (0.01%) | 5.0 |
| D | PRESERVATIVES | 0.5 |
| D | LECITHIN | 0.4 |

Example 11

Prophetic

Preparation of Liposomes Containing Ac-L-Arg-Phg-L-Val-Phg-OH.

Dipalmitoylphosphatidylcholine (DPPC) is weighed and dissolved in chloroform.

The solvent is evaporated under vacuum until a thin layer of phospholipid is obtained, and this layer is hydrated by treatment at 55° C. with an aqueous solution of the peptide to the desired concentration (containing Phenonip®), and MLV liposomes are obtained. ULV liposomes are obtained by immersing MLV liposomes in an ultrasonic bath at 55° C. for 8 cycles of 2 min at 5 min intervals. The size of ULV liposomes is reduced by passing them through an extrusion system at high pressure.

| INGREDIENT (INCI Nomenclature) | % IN WEIGHT |
|---|---|
| PHOSPHATIDYLCHOLINE | 4.0 |
| Ac-L-Arg-Phg-L-Val-Phg-OH | 0.2 |
| PRESERVATIVES | 0.50 |
| AQUA (WATER) | q.s.p. 100 |

Example 12

Prophetic

Composition of a Facial Cream Containing Ac-Phg-Phg-L-Trp-Phg-OH.

| | INGREDIENT (INCI Nomenclature) | % IN WEIGHT |
|---|---|---|
| A | BUTYROSPERMUM PARKII | 3.5-4.5 |
| A | CETEARYL ETHYLHEXANOATE | 3-5 |
| A | GLYCERYL STEARATE S.E. | 1.5-2.5 |
| A | SQUALANE | 0.5-1 |
| A | PEG-100 STEARATE | 1 |
| A | POLYSORBATE 60 | 0.30 |
| A | CETYL PALMITATE | 1.5-2.5 |
| A | DIMETHICONE | 2.5-3.5 |
| A | CETEARYL ALCOHOL | 1.5-2.5 |
| A | PALMITIC ACID | 0.5 |
| B | AQUA (WATER) | 2 |
| B | GLYCERIN | 1.5-2.5 |
| B | BUTYLENE GLYCOL | 1-3 |
| B | MANNITOL | 0.5-1.5 |
| B | HYDROGENATED LECITHIN | 0.5-1.5 |
| B | PROPYLENE GLYCOL | 0.5-1.5 |
| C | CARBOMER | 0.4 |
| C | ETHYLHEXYL PALMITATE | 1.5-2.5 |
| D | TROMETHAMINE | 0.4 |
| D | AQUA (WATER) | 1 |
| E | PRESERVATIVES | q.s. |
| F | Ac-Phg-Phg-L-Trp-Phg-OH | 0.001 |
| F | AQUA (WATER) | q.s.p.100 |

Example 13

Prophetic

Preparation of a Composition in the Form of a Liposome Gel Containing Ac-L-Arg-Phg-L-Val-Phg-OH.

The liposomes of example 11 are dispersed in water with preservatives (EDTA, imidazolidinyl urea and Phenonip®) under gentle stirring. Hispagel® 200 is added [INCI: Water, glycerin, glyceryl polyacrylate] and stirred gently until a homogeneous mixture is obtained.

| INGREDIENT (INCI Nomenclature) | % IN WEIGHT |
|---|---|
| LIPOSOMES CONTAINING Ac-L-Arg-Phg-L-Val-Phg-OH (1%) | 10.00 |
| DISODIUM EDTA | 0.15 |
| IMIDAZOLIDINYL UREA | 0.10 |

-continued

| INGREDIENT (INCI Nomenclature) | % IN WEIGHT |
|---|---|
| PRESERVATIVE | 0.50 |
| AQUA (WATER) | 29.25 |
| AQUA (WATER), GLYCERIN, GLYCERYL POLYACRYLATE | 60.00 |

Example 14

Prophetic

Composition of a Microemulsion Containing Ac-L-Arg-Phg-L-Trp-Phg-OH.

| INGREDIENT (INCI Nomenclature) | % IN WEIGHT |
|---|---|
| DIETHYLHEXYL SODIUM SULFOSUCCINATE | 1.35 |
| ISOSTEARIC ACID | 7.65 |
| AQUA (WATER) | 0.2 |
| ALCOHOL DENAT | 0.8 |
| ETHYLHEXYL COCOATE | 90 |
| Ac-L-Arg-Phg-L-Trp-Phg-OH | 0.005 |

Example 15

Composition of a Body Gel Containing Ac-L-Arg-Phg-L-Trp-Phg-OH.

| INGREDIENT (INCI Nomenclature) | % IN WEIGHT |
|---|---|
| AQUA (WATER) | q.s.p. 100 |
| PRESERVATIVES | 0.5 |
| PERFUME (FRAGRANCE) | 0.10 |
| DENATURATED ALCOHOL | 10.0 |
| ACRYLATES/C10-30 ALKYL ACRYLATE CROSSPOLYMER | 0.75 |
| LECITHIN | 0.12 |
| BUTYLENEGLYCOL | 0.75 |
| Ac-L-Arg-Phg-L-Trp-Phg-OH | 0.0003 |
| XANTHAN GUM | 0.012 |

Example 16

Prophetic

Composition of a Hair Lotion Containing Ac-L-Arg-Phg-L-Trp-Phg-NH—(CH$_2$)$_{15}$—CH$_3$.

| INGREDIENT (INCI Nomenclature) | % IN WEIGHT |
|---|---|
| DENATURATED ALCOHOL | 50-60 |
| PANTHENOL | 0.05-0.15 |
| ZINC RICINOLEATE | 0.05-0.10 |
| FRAGRANCE | 0.02 |
| AQUA (WATER) | q.s.p.100 |
| Ac-L-Arg-Phg-L-Trp-Phg-NH—(CH$_2$)$_{15}$—CH$_3$ | 0.01 |

Example 17

Prophetic

Preparation of a Composition of Mixed Micelles Containing Ac-L-Arg-Phg-L-Trp-Phg-OH.

In a vessel suitable for the entire sample the ingredients of phase A are weighed and warmed slightly to about 30° C. to help dissolve some of the preservatives. Next, phase B components are added and homogenized under moderate stirring.

Phase C is then added under continuous stirring, after which phase D is added with slow stirring to avoid foaming.

The pH is adjusted to 5.5-6.5.

| | INGREDIENT (INCI Nomenclature) | % IN WEIGHT |
|---|---|---|
| A | AQUA (WATER) | q.s.p.100 |
| A | PHENOXYETHANOL | 0.5 |
| A | CAPRILYL GLYCOL | 0.5 |
| A | POTASSIUM SORBATE | 0.3 |
| B | AQUA (WATER) | 27.5 |
| B | Ac-L-Arg-Phg-L-Trp-Phg-OH | 0.025 |
| B | LECITHIN | 4.0 |
| C | XANTHAN GUM | 0.4 |
| D | AQUA (WATER). CAPRILYL/CAPRYL GLUCOSIDE | 30 |

Example 18

Effect of the Composition of Example 15 on the Increase of Skin Elasticity.

To evaluate the effectiveness of the composition of Example 15 of the invention, the lotion was applied on the thighs of 20 volunteers twice daily for two months.

Skin elasticity was measured using a Cutometer and the results obtained are shown in Table 4.

TABLE 4

| Measurement of skin elasticity | | | | |
|---|---|---|---|---|
| Measurement of maximum deformation ($R_0$) | | | | |
| $T_0$ | $T_f$ | Average variation | % Variation | t-Student |
| 0.256 | 0.216 | −0.04 | −15.6% | $p < 0.001$ |
| Measurement of elasticity ($R_2$) | | | | |
| $T_0$ | $T_f$ | Average change | % Variation | t-Student |
| 0.572 | 0.652 | 0.08 | 14.0% | $p < 0.001$ |

An average increase of 14% in the elasticity was obtained.

Example 19

Effect of a Placebo Composition Corresponding to the Composition of Example 15 on the Increase of Skin Elasticity.

To evaluate the effectiveness of a placebo composition corresponding to the composition of Example 15 of the invention (without the peptide Ac-L-Arg-Phg-L-Trp-Phg-OH), a panel of 20 volunteers applied the lotion on the thighs twice daily for two months.

Skin elasticity was measured using a Cutometer and the results obtained are shown in Table 5.

TABLE 5

| Measurement of skin elasticity | | | | |
|---|---|---|---|---|
| Measurement of maximum deformation ($R_0$) | | | | |
| $T_0$ | $T_f$ | Average variation | % Variation | t-Student |
| 0.243 | 0.234 | −0.009 | −3.7% | p > 0.05 |
| Measurement of elasticity ($R_2$) | | | | |
| $T_0$ | $T_f$ | Average change | % Variation | t-Student |
| 0.584 | 0.567 | −0.017 | −2.9% | p > 0.05 |

No increase in skin elasticity was observed after two months treatment.

Example 20

Collagen Synthesis Stimulation Assay.

Human dermal fibroblasts were grown until confluence in MI06 medium supplemented with specific growth factors for fibroblasts. Then, they were strypsinised and seeded at $5 \times 10^4$ cells/well in 24-well plates. After 24 h of incubation at 37° C. in 5% $CO_2$ atmosphere, fresh medium was added with scalar dilutions of the peptides at 15 µg/ml or with vehicle as negative control. Cells were incubated for 48 additional hours, after which medium was collected.

The analysis of the amount of secreted Collagen Type I was performed by means of an ELISA assay. Briefly, 96-well plated were coated with 50 µL per well of the previously collected medium and allowed to adsorb overnight at 4° C. in a humidified atmosphere. Then the plates were washed 3 times with PBS (+0.05% Tween-20) and blocked for 1 h with 3% BSA. After blocking, the plates were treated with an anti-Collagen Type I antibody (1:1000 in PBS, 0.05% Tween-20, 1% BSA) for 2 h. After this incubation, the secondary antibody (goat anti-mouse IgG-HRP antibody, Molecular Probes, 1:1000 in PBS, 0.05% Tween-20, 1% BSA) was added. Plates were incubated with phosphatase substrate for 30 min and the reaction was stopped by adding 3 M $H_2SO_4$. Absorbance at 490 nm was read using a microplate reader and collagen concentration determined using a linear regression standard curve for Collagen Type I. Values were normalized in respect to the collagen values for the negative control experiment and the increase in the Collagen Type I was calculated for all the treatments. Table 6 lists calculated values for the increase of Collagen Type I content.

TABLE 6

| Increase of Collagen Type I by treatment with the peptides | |
|---|---|
| Peptide | Increase |
| Control | 0% |
| H-L-Arg-Phg-L-Val-Phg-OH | 18% |
| H-L-Arg-Phg-L-Val-Gly-OH | 16% |
| H-L-Arg-Phg-L-Trp-Phg-OH | 99% |

The invention claimed is:

1. A peptide of general formula (I)

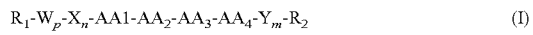

$$R_1\text{-}W_p\text{-}X_n\text{-}AA1\text{-}AA_2\text{-}AA_3\text{-}AA_4\text{-}Y_m\text{-}R_2 \quad (I)$$

its stereoisomers, mixtures thereof, and/or its cosmetically or pharmaceutically acceptable salts, wherein at least one of the amino acids $AA_1$, $AA_2$ and $AA_4$ is uncoded, and in that:

$AA_1$ is selected from the group consisting of -Arg-, -Phg- and -Nle- or is a bond;

$AA_2$ is selected from the group consisting of -Ala-, -Phg-, -Cit- and -Nle-;

$AA_3$ is selected from the group consisting of -Trp-, -Val- and -Tyr-;

$AA_4$ is selected from the group consisting of -Phg- and -Gly-;

W, X and Y are independently selected from the group consisting of coded or uncoded amino acids;

p, n and m range between 0 and 1;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO;

$R_2$ is selected from the group consisting of —$NR_3R_4$, —$OR_3$ and —$SR_3$;

wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl and substituted or unsubstituted aralkyl;

wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

and provided that when $AA_1$ is a bond, $AA_2$ is -Phg- and $AA_3$ is -Tip-.

2. The peptide according to claim 1, wherein $R_1$ is selected from the group consisting of H and $R_5$—CO—, wherein $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl with 2 to 24 carbon atoms and 1 to 3 atoms other than carbon and an alkyl chain of 1 to 6 carbon atoms.

3. The peptide according to claim 2, wherein $R_1$ is selected from the group consisting of H, acetyl, tert-butanoyl, hexanoyl, 2-methylhexanonyl, cyclohexancarboxyl, octanoyl, decanoyl, lauroyl, myristoyl, palmitoyl, stearoyl, oleoyl and linoleoyl.

4. The peptide according to claim 1, wherein $R_2$ is —$NR_3R_4$ or $OR_3$, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl with 2 to 24 carbon atoms and 1 to 3 atoms other than carbon and an alkyl chain of 1 to 6 carbon atoms.

5. The peptide according to claim 4, wherein $R_3$ and $R_4$ are independently selected from the group consisting of H, methyl, ethyl, hexyl, dodecyl and hexadecyl.

6. The peptide according to claim 1, wherein $R_1$ is selected from the group consisting of H, acetyl, lauroyl, myristoyl and palmitoyl, $AA_1$ is -L-Arg- or -L-Nle-, $AA_2$ is -L-Phg- or -D-Phg-, $AA_3$ is -L-Tyr-, $AA_4$ is -L-Phg- or -D-Phg- and $R_2$ is —$NR_3R_4$ or —$OR_3$ wherein $R_3$ and $R_4$ are independently selected from H, methyl, ethyl, hexyl, dodecyl and hexadecyl.

7. The peptide according to claim 1, wherein $R_1$ is selected from the group consisting of H, acetyl, lauroyl, myristoyl or palmitoyl, $AA_1$ is -L-Arg- or -L-Nle- or a bond, $AA_2$ is -L-Phg- or -D-Phg-, $AA_3$ is -L-Trp-, $AA_4$ is -L-Phg- or -D-Phg-, and $R_2$ is —$NR_3R_4$ or —$OR_3$ wherein $R_3$ and $R_4$ are independently selected from H, methyl, ethyl, hexyl, dodecyl and hexadecyl.

8. The peptide according to claim 1, wherein $R_1$ is selected from the group consisting of H, acetyl, lauroyl, myristoyl or palmitoyl, $AA_1$ is -L-Arg-, $AA_2$ is -L-Phg- or -D-Phg-, $AA_3$ is -L-Val-, $AA_4$ is -L-Phg- or -D-Phg- or -L-Gly-, and $R_2$ is —$NR_3R_4$ or —$OR_3$ wherein $R_3$ and $R_4$ are independently selected from H, methyl, ethyl, hexyl, dodecyl and hexadecyl.

9. The peptide according to claim 1, wherein $R_1$ is selected from the group consisting of H, acetyl, lauroyl, myristoyl or palmitoyl, $AA_1$ is -L-Phg- or -D-Phg-, $AA_2$ is -L-Phg- or -D-Phg-, $AA_3$ is -L-Trp-, $AA_4$ is -L-Phg- or -D-Phg-, and $R_2$ is —$NR_3R_4$ or —$OR_3$ wherein $R_3$ and $R_4$ are independently selected from H, methyl, ethyl, hexyl, dodecyl and hexadecyl.

10. A process for preparation of a peptide of general formula (I), its stereoisomers, mixtures thereof, and/or its cosmetically or pharmaceutically acceptable salts according to claim 1, comprising synthesizing said peptide on solid phase or in solution phase.

11. Cosmetic or pharmaceutical composition including a cosmetically or pharmaceutically effective amount of at least one peptide of general formula (I), its stereoisomers, mixtures thereof and/or its cosmetically or pharmaceutically acceptable salts, according to claim 1, and at least one excipient or cosmetically or pharmaceutically acceptable adjuvant.

12. The composition according to claim 11, wherein the peptide of general formula (I) is at a concentration of between 0.000001% and 20% in weight, with respect to the total weight of the composition.

13. The composition according to claim 11, wherein the peptide of general formula (I), its stereoisomers, mixtures thereof and/or its cosmetically or pharmaceutically acceptable salts, is incorporated into a cosmetic or pharmaceutically acceptable delivery system or sustained release system selected from the group consisting of liposomes, mixed liposomes, oleosomes, niosomes, millicapsules, microcapsules, nanocapsules, sponges, cyclodextrins, vesicles, micelles, mixed micelles of surfactants, surfactant-phospholipid mixed micelles, millispheres, microspheres, nanospheres, liposheres, microemulsions, nanoemulsions, miniparticles, milliparticles, microparticles, nanoparticles and solid lipid nanoparticles or is adsorbed on a cosmetically or pharmaceutically acceptable solid organic polymer or solid mineral substrate selected from the group consisting of talc, bentonite, silica, starch or maltodextrin.

14. The composition according to claim 11, wherein said composition is a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, tablets, sugar coated tablets, granules, chewing gums, solutions, suspensions, emulsions, syrups, polysaccharide films, jellies and gelatines.

15. The composition according to claim 11, wherein said composition is a product selected from the group consisting of concealers, makeup foundations, makeup removal lotions, makeup removal milks, eye shadows, lipsticks, lip glosses, lip protectors and powders.

16. The composition according to claim 11, wherein the peptide of general formula (I), its stereoisomers, mixtures thereof and/or its cosmetically or pharmaceutically acceptable salts is incorporated in a fabric, a non-woven fabric or a medical device.

17. The composition according to claim 11, wherein said composition further comprises a cosmetically or pharmaceutically effective amount of at least one adjuvant selected from the group of elastase inhibiting agents, matrix metalloprotease inhibiting agents, melanin synthesis stimulating or inhibiting agents, whitening or depigmenting agents, propigmenting agents, self-tanning agents, antiaging agents, inhibiting agents of NO-synthase, inhibiting agents of 5α-reductase, inhibiting agents of lysyl- and/or prolyl-hydroxylase, antioxidants, free radical scavengers and/or agents against atmospheric pollution, reactive carbonyl species scavengers, anti-glycation agents, antihistamine agents, antiemetic agents, antiviral agents, antiparasitic agents, emulsifiers, emollients, organic solvents, liquid propellants, skin conditioners, humectants, substances that retain moisture, alpha hydroxyacids, beta hydroxyacids, moisturizers, epidermal hydrolytic enzymes, vitamins, pigments or colorants, dyes, gelling polymers, thickeners, surfactants, softening agents, anti-wrinkle agents, agents able to reduce or treat the bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, agents stimulating collagen synthesis, agents stimulating the synthesis of elastin, agents stimulating the synthesis of decorin, agents stimulating the synthesis of laminin, agents stimulating the synthesis of defensins, agents stimulating the synthesis of chaperones, agents stimulating the synthesis of aquaporins, agents stimulating the synthesis of hyaluronic acid, agents stimulating the synthesis of fibronectin, agents stimulating the synthesis of sirtuins, agents stimulating the synthesis of lipids and components of the stratum corneum, agents stimulating the synthesis of ceramides, agents that inhibit collagen degradation, agents that inhibit elastin degradation, agents that inhibit serine proteases such cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, agents stimulating the synthesis of glycosaminoglycans, antihyperkeratosis agents, comedolytic agents, antipsoriasis agents, DNA repairing agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, preservatives, perfumes, chelating agents, vegetable extracts, essential oils, marine extracts, agents obtained from a biofermentation process, mineral salts, cell extracts and sunscreens, organic or mineral photoprotective agents active against A and/or B ultraviolet rays or a mixture thereof.

18. A cosmetic or pharmaceutical method for the treatment and/or care of skin, mucous membranes and/or scalp which comprises topically or transdermally administering an effective amount of at least one peptide of general formula (I), its stereoisomers, mixtures thereof, and/or its cosmetically or pharmaceutically acceptable salts, according to claim 1.

19. The cosmetic or pharmaceutical method according to claim 18 for the treatment and/or care of those conditions, disorders and/or diseases of skin, mucous membranes and/or scalp which are the result of elastase activity.

20. The cosmetic or pharmaceutical method according to claim 18 for the treatment and/or care of those conditions, disorders and/or diseases of skin, mucous membranes and/or scalp which benefit from stimulation of collagen synthesis.

21. The cosmetic or pharmaceutical method according to claim 18 in which said treatment and/or care increases skin elasticity.

22. The cosmetic or pharmaceutical method according to claim 18 in which said treatment and/or care reduces or eliminates facial wrinkles.

23. The cosmetic or pharmaceutical method according to claim 19 in which the conditions, disorders and/or diseases are selected from the group consisting of wrinkles, expression wrinkles, stretch marks, skin aging, skin photoaging, wound healing disorders, ulcers, diabetic ulcers, keloids, hypertrophic scars, acne, cellulite, orange peel skin, elastosis, actinic elastosis, keratosis, inflammation, dermatitis, atopic dermatitis, allergic dermatitis, sensitive skin, eczema, bullous pemphigoid, gingivitis, periodontitis, skin cancer, tumor invasions, tumour metastasis, telangiectasia, couperosis, varicose veins, eye dark circles, bags under the eye, alopecia and hair loss, rosacea, and/or psoriasis.

24. The cosmetic or pharmaceutical method according to claim 20 in which the conditions, disorders and/or diseases are selected from the group consisting of wrinkles, expression wrinkles, stretch marks, skin aging, skin photoaging, wound healing disorders, ulcers, diabetic ulcers, keloids, hypertrophic scars, acne, cellulite, orange peel skin, elastosis, actinic elastosis, keratosis, inflammation, dermatitis, atopic dermatitis, allergic dermatitis, sensitive skin, eczema, bullous pemphigoid, gingivitis, periodontitis, skin cancer, tumor invasions, tumour metastasis, telangiectasia, couperosis, varicose veins, eye dark circles, bags under the eye, alopecia and hair loss, rosacea, and/or psoriasis.

25. The cosmetic or pharmaceutical method according to claim 18 in which said treatment and/or care reduces and/or delays the signs of aging and/or photoaging.

* * * * *